United States Patent
Nakao

(10) Patent No.: US 9,713,465 B1
(45) Date of Patent: Jul. 25, 2017

(54) SURGICAL CLOSURE DEVICE AND ASSOCIATED METHOD

(75) Inventor: Naomi L Nakao, New York, NY (US)

(73) Assignee: GRANIT MEDICAL INNOVATION LLC, New York, NY (US)

( * ) Notice: Subject to any disclaimer, the term of this patent is extended or adjusted under 35 U.S.C. 154(b) by 1962 days.

(21) Appl. No.: 11/434,627

(22) Filed: May 16, 2006

Related U.S. Application Data

(63) Continuation-in-part of application No. 11/109,004, filed on Apr. 19, 2005, now Pat. No. 7,833,238.

(60) Provisional application No. 60/563,534, filed on Apr. 19, 2004.

(51) Int. Cl.
*A61B 17/04* (2006.01)

(52) U.S. Cl.
CPC ...... *A61B 17/0469* (2013.01); *A61B 17/0401* (2013.01); *A61B 2017/0472* (2013.01)

(58) Field of Classification Search
CPC ......... A61B 17/02; A61B 17/03; A61B 17/04; A61B 17/06; A61B 17/08; A61B 17/122; A61B 17/128; A61B 17/0469; A61B 17/0482; A61B 17/0401; A61B 17/10; A61B 17/072; A61B 2017/0472; A61B 2017/0488; A61B 2017/0409; A61M 25/0082; A61M 25/0084; A61M 25/0662
USPC ........ 606/151–153, 232, 139, 142, 143, 144
See application file for complete search history.

(56) References Cited

U.S. PATENT DOCUMENTS

| | | | |
|---|---|---|---|
| 643,003 A | 2/1900 | Pollock | |
| 943,263 A | 12/1909 | Moraneck | |
| 1,510,416 A | 9/1924 | Pietz et al. | |
| 2,113,246 A | 4/1938 | Wappler | |
| 2,968,041 A | 1/1961 | Skold | |
| 3,378,010 A | 4/1968 | Codling et al. | |
| 3,518,993 A | 7/1970 | Blake | |
| 3,875,648 A * | 4/1975 | Bone | 29/417 |
| 3,882,854 A | 5/1975 | Hulka et al. | |
| 3,958,576 A | 5/1976 | Komiya | |
| 4,038,987 A | 8/1977 | Komiya | |
| 4,367,746 A | 1/1983 | Sandhaus | |
| 4,446,865 A | 5/1984 | Jewusiak | |
| 4,485,817 A | 12/1984 | Swiggett | |
| 4,493,323 A * | 1/1985 | Albright et al. | 606/144 |
| 4,496,090 A | 1/1985 | Ceriver et al. | |
| 4,627,437 A * | 12/1986 | Bedi et al. | 606/220 |
| 4,669,473 A * | 6/1987 | Richards et al. | 606/215 |
| 4,681,107 A | 7/1987 | Kees | |
| 4,706,668 A | 11/1987 | Backer | |
| 4,714,075 A | 12/1987 | Krauter et al. | |
| 4,735,194 A | 4/1988 | Stiegmann | |
| 4,736,746 A * | 4/1988 | Anderson | 606/220 |
| 4,759,364 A | 7/1988 | Boebel | |
| 4,796,627 A | 1/1989 | Tucker | |
| 4,821,721 A | 4/1989 | Chin et al. | |

(Continued)

*Primary Examiner* — Dianne Dornbusch
(74) *Attorney, Agent, or Firm* — R. Neil Sudol; Henry D. Coleman

(57) ABSTRACT

A surgical fastening assembly has a fastener delivery sub-assembly with a plurality of elongated tubular needle members rigidly affixed to one another about a longitudinal axis of the subassembly. The tubular needle members are positionable around an elongate trocar movably positionable inside a cannula. The cannula is coupled to the fastener delivery sub-assembly. Anchors or fasteners are disposed in the needle members and ejected at the same time by a pusher member.

1 Claim, 42 Drawing Sheets

(56) References Cited

U.S. PATENT DOCUMENTS

| | | | |
|---|---|---|---|
| 4,841,888 A | 6/1989 | Mills et al. | |
| 4,880,015 A | 11/1989 | Nierman | |
| 4,887,612 A | 12/1989 | Esser et al. | |
| 4,934,364 A | 6/1990 | Green | |
| 4,945,920 A | 8/1990 | Clossick | |
| 4,971,067 A | 11/1990 | Bolduc et al. | |
| 4,983,176 A | 1/1991 | Cushman et al. | |
| 5,015,249 A | 5/1991 | Nakao et al. | |
| 5,022,126 A | 6/1991 | Davis | |
| 5,032,127 A | 7/1991 | Frazee et al. | |
| 5,049,153 A | 9/1991 | Nakao et al. | |
| 5,156,609 A | 10/1992 | Nakao et al. | |
| 5,222,961 A | 6/1993 | Nakao et al. | |
| 5,304,184 A * | 4/1994 | Hathaway | A61B 17/0057 606/144 |
| 5,312,391 A * | 5/1994 | Wilk | A61B 17/00234 604/264 |
| 5,368,601 A * | 11/1994 | Sauer et al. | 606/144 |
| 5,391,182 A * | 2/1995 | Chin | A61B 17/0469 128/898 |
| 5,476,470 A * | 12/1995 | Fitzgibbons, Jr. | A61B 17/06109 606/139 |
| 5,478,353 A | 12/1995 | Yoon | |
| 5,496,332 A * | 3/1996 | Sierra | A61B 17/0057 606/139 |
| 5,573,540 A * | 11/1996 | Yoon | A61B 17/0469 606/139 |
| 5,573,543 A | 11/1996 | Akopov | |
| 5,695,504 A * | 12/1997 | Gifford et al. | 606/153 |
| 5,700,273 A * | 12/1997 | Buelna | A61B 17/04 606/144 |
| 5,707,342 A * | 1/1998 | Tanaka | A61B 1/0008 600/114 |
| 5,836,955 A * | 11/1998 | Buelna | A61B 17/04 606/144 |
| 5,893,856 A | 4/1999 | Jacob et al. | |
| 5,961,539 A | 10/1999 | Northrup et al. | |
| 5,997,515 A * | 12/1999 | de la Torre | A61B 17/3417 604/246 |
| 6,004,303 A * | 12/1999 | Peterson | A61B 17/3439 604/167.01 |
| 6,110,185 A * | 8/2000 | Barra et al. | 606/148 |
| 6,203,554 B1 * | 3/2001 | Roberts | 606/144 |
| 6,206,895 B1 * | 3/2001 | Levinson | A61B 17/0057 606/144 |
| 6,287,317 B1 * | 9/2001 | Makower et al. | 606/153 |
| 6,328,730 B1 * | 12/2001 | Harkrider, Jr. | A61B 17/3421 600/130 |
| 6,352,503 B1 * | 3/2002 | Matsui | A61B 1/00071 600/104 |
| 6,358,258 B1 * | 3/2002 | Arcia et al. | 606/139 |
| 6,364,897 B1 | 4/2002 | Bonutti | |
| 6,626,930 B1 * | 9/2003 | Allen | A61B 17/0401 606/213 |
| 6,986,775 B2 | 1/2006 | Morales et al. | |
| 7,029,435 B2 * | 4/2006 | Nakao | A61B 1/00071 600/104 |
| 7,029,481 B1 * | 4/2006 | Burdulis et al. | 606/148 |
| 7,094,244 B2 * | 8/2006 | Schreck | A61B 17/00234 128/898 |
| 7,153,314 B2 * | 12/2006 | Laufer et al. | 606/153 |
| 7,186,262 B2 | 3/2007 | Saadat | |
| 7,588,557 B2 * | 9/2009 | Nakao | A61B 17/221 604/164.01 |
| 7,722,633 B2 * | 5/2010 | Laufer et al. | 606/153 |
| 7,753,924 B2 | 7/2010 | Starksen | |
| 7,850,600 B1 * | 12/2010 | Piskun | A61B 1/05 600/114 |
| 7,967,842 B2 * | 6/2011 | Bakos | A61B 17/0057 600/104 |
| 7,993,405 B2 * | 8/2011 | Cauthen, III | A61F 2/441 606/86 R |
| 8,317,679 B2 * | 11/2012 | Surti | A61B 17/0057 600/104 |
| 8,715,294 B2 * | 5/2014 | Ortiz | A61B 1/2736 606/108 |
| 8,753,262 B2 * | 6/2014 | Sugiyama | A61B 1/00193 600/104 |
| 2003/0130560 A1 * | 7/2003 | Suzuki et al. | 600/104 |
| 2003/0130561 A1 * | 7/2003 | Suzuki | A61B 1/00098 600/107 |
| 2003/0144694 A1 * | 7/2003 | Chanduszko et al. | 606/213 |
| 2004/0122456 A1 * | 6/2004 | Saadat et al. | 606/157 |
| 2005/0075654 A1 | 4/2005 | Kelleher | |
| 2005/0216028 A1 * | 9/2005 | Hart | A61B 17/3498 606/108 |
| 2006/0015006 A1 * | 1/2006 | Laurence et al. | 600/104 |
| 2006/0064115 A1 * | 3/2006 | Allen et al. | 606/139 |
| 2006/0074374 A1 * | 4/2006 | Gresham | A61B 17/3474 604/26 |
| 2007/0112425 A1 * | 5/2007 | Schaller et al. | 623/2.37 |
| 2007/0270752 A1 * | 11/2007 | LaBombard | A61B 1/00154 604/164.01 |
| 2008/0294001 A1 * | 11/2008 | Surti | A61B 17/0057 600/104 |

* cited by examiner

SURGICAL CLOSURE DEVICE AND ASSOCIATED METHOD

CROSS-REFERENCE TO RELATED APPLICATION

This application is a continuation-in-part of application Ser. No. 11/109,004 filed Apr. 19, 2005. This application also claims the benefit of U.S. Provisional Application No. 60/563,534, filed on Apr. 19, 2004, which application is incorporated herein by reference in its entirety.

FIELD OF THE INVENTION

The present invention relates to a surgical fastening device and associated surgical anchors. The invention also relates to associated surgical methodology employing such instruments or devices. The invention is more specifically related in part to a surgical fastening device or assembly delivers multiple fasteners in one maneuver in order to approximate tissue together.

BACKGROUND OF THE INVENTION

Surgery in the abdomen is presently performed through an incision that permits access to the operative site (laparotomy), or through rigid cannulas inserted into small incisions in the abdominal wall as visualized by a camera (laparoscopy). There is no reliable device or method for sewing or stapling through a flexible endoscope. Such procedures are primarily diagnostic in nature with the exception of biopsy and polypectomy. Recently there has been increasing interest in devising methods for performing surgery via the flexible endoscope inserted through a natural orifice. The potential advantages that such procedures might offer are related to their being even more minimally invasive than laparoscopic surgery, decreasing morbidity and discomfort. This scenario would be especially advantageous in the morbidly obese patient, who presents an even larger operative challenge than a patient of normal weight. In addition, if such procedures were made possible, certain operations to treat morbid obesity performed through a natural orifice may become possible.

Morbid obesity has reached epidemic proportions in the United States, affecting more than 30% of adults. The prevalence of obesity has been rising steadily, resulting in significant chronic health problems and nearly 300,000 deaths per year. Obesity and its associated health problems have substantial economic consequences for the United States health care system; in 1995, the total costs attributable to obesity were estimated at $99 billion. Bariatric surgery is the most effective treatment modality, and has been recognized by the National Institutes of Health as the only successful long-term treatment.

The Roux-en-Y gastric bypass operation considered the standard of surgical care, is a long and risky operation whether performed laparoscopically or through laparotomy. Because of the increased risk entailed in this operation, gastric restrictive operations have been performed in increasing numbers. These operations are intended to restrict food intake without removing any gastric tissue, or bypassing intestine. While less traumatic, significant convalescence time and complications still prevail.

Providing a method and accompanying device for performing surgery in conjunction with a flexible endoscope may reduce the length and complexity of abdominal operations, possibly decreasing morbidity and mortality, shortening hospital stay, and providing cost savings.

Transgastric surgery has been attempted, but has not yet been successful in humans, primarily because there is no reliable device to enable closing of the incision through the flexible endoscope. If this were to be made possible, instruments could be introduced through a natural orifice, for example the mouth, and then brought through an incision in the stomach. In this way surgery could be performed in the abdominal cavity eliminating necessity for external incisions.

Conventional surgery often necessitates the use of clips, staples, or other surgical fasteners. Such procedures generally require that an extensive incision be made (open surgery), or that a series of small incisions be created, through which several cannulas are placed for providing access to a body cavity (laparoscopic surgery).

Currently, there is no reliable method for securing clips, staples, or other surgical fasteners inside a patient's body in conjunction with a flexible endoscope. The challenge entailed in creating a fastener and a delivery and deployment device that may be passed through a flexible endoscope is two-fold: firstly, the working channel of an endoscope is very narrow requiring a device with an outer diameter sufficiently small to pass through it. Secondly, a flexible endoscope bends along with curvatures of the internal body lumens, requiring similar flexibility of a fastener delivery and deployment device to enable such a journey. Both of these challenges have not yet been surmounted; hence there are no such devices currently available. Suturing operations have similar limitations, and as such physicians have been unable to perform surgical procedures via natural body orifices using a flexible endoscope.

When performing a procedure with an instrument passed through a flexible endoscope, the simplest method to operate this instrument is through either a pushing, or pulling motion performed proximally by the operator. As the surgical instruments traverse bends in the endoscope, a turning or torquing motion performed proximally does not translate in a 1:1 ratio distally. Pushing or pulling, on the other hand is ergonomically simpler for the operator, and is transmitted through the entire instrument better. Therefore, most procedures performed through the flexible endoscope, such as biopsy, or polypectomy, employ a push or a pull action at the handle, or proximal aspect of the instrument. It would therefore be advantageous to provide a device that would enable application of fasteners through a simple push of the extracorporeal, proximal aspect of the fastener application device.

Laparoscopic surgery has been developing rapidly in the past few years because it is less invasive than open surgery. These procedures enable sewing or stapling tissue via a series of small abdominal incisions through which a number of cannulas are placed. Rigid instruments are passed through these cannulas and manipulated from outside the body. The surgical procedure is visualized with a camera, which is introduced through a separate cannula.

Providing smaller diameter instruments capable of reaching surgical sites through smaller access ports or cannulas would provide an advantage during laparoscopic surgery because smaller incisions cause a lesser injury, providing for a more rapid healing process. The size of the instruments used to deliver surgical staples, for example, is dictated by staple size.

The currently used staple delivery device sizes have been decreased by designing the device for delivery of a closed staple. This enables passage of these devices through smaller diameter cannulas. Upon reaching the operative site, such a staple must be opened by some means, in order to engage a target tissue, after which the staple is again closed upon the tissue. Consequently, a staple may be displaced, or slip out of the delivery device's jaws. Furthermore, the force required to open and close the staple or clip is magnified because it is transmitted through the distance of the shaft. Providing an anchoring system that would permit introduction and delivery of an anchor in a substantially closed configuration, would preclude a need for the "closed open closed" design.

Although there appear to be no commercial devices on the market that enable stapling through the working channel of the flexible endoscope, U.S. Pat. Nos. 5,222,961, 5,156,609, 5,015,249 and 5,049,153 to Nakao et al. describe various embodiments of an endoscopic stapling device. U.S. Pat. No. 5,015,249 describes a flexible stapler whereby the staple is configured with an open bias, and releasably connected to a rod member. The staple is ejected by pushing the rod member forward. Upon engagement of the staple with tissue, the staple being opened by its open bias, a tubular member is pushed over the staple to close it. The problem with the embodiment of the '249 patent is the following: bowel wall thickness, for example, is approximately 0.5 cm, and its consistency is slightly firmer than that of a calfs liver. Closing an indwelling staple by pushing a tubular member over it may push the entire staple through the bowel wall.

U.S. Pat. No. 5,049,153 describes a flexible stapler, wherein a staple with an open bias is disposed in the prefiring position inside said stapler's open jaws. The stapler is brought to the tissue with the indwelling staple, closed upon the tissue, and once the staple locks, the staple legs are released. U.S. Pat. No. 5,156,609 describes a plurality of second staples each having a spring bias. U.S. Pat. No. 5,222,961 describes various additional means of locking a staple. All the above-mentioned patents address staples to be delivered by an endoscopic stapler. The invention disclosed herein describes an anchoring device and an instrument for delivering one or more anchors held together by a suture thread or another line element. This device assembly is designed quite differently than the staplers described above.

OBJECTS OF THE INVENTION

It is an object of the present invention to provide a surgical fastening assembly applying one or more surgical anchors to enable closure of an incision or opening in organic tissue.

A more specific object of the present invention is to provide such a surgical fastening assembly wherein the deployment of multiple surgical fasteners or anchors is facilitated.

Another specific object of the present invention is to provide such a surgical fastening assembly wherein the surgical fasteners or anchors are inserted through relatively small incisions into or through organic tissues of a patient.

It is a further object of the present invention to provide an anchoring system whereby the anchor(s) may remain in a substantially closed configuration throughout the entire fastening operation, and assumes an open configuration only when deployed into tissue.

It is also desirable to provide an anchoring system, which is ergonomically beneficial because it can be operated extracorporeally through a pushing operation.

Another object of the present invention is to provide a surgical fastening assembly that is utilizable in interactive or translumenal surgery to close incisions in hollow internal body organs such as the stomach. It is desirable to enable tissue fastening performed in conjunction with an endoscope, primarily though not exclusively through existing body orifices.

Further objects of the present invention pertain to providing new methods for surgical procedures wherein closures of incisions and perforations are facilitated.

These and other objects of the present invention will be apparent from the drawings and descriptions herein. Although every object of the invention is believed to be attained by at least one embodiment of the invention, there is not necessarily any single embodiment that achieves all of the objects of the invention.

SUMMARY OF THE INVENTION

The present invention is directed to a surgical fastening assembly and an associated closure method that are useful in a variety of surgical procedures including endoscopic and laparoscopic operations and interactive endoscopic procedures involving both flexible endoscopes inserted through a natural body orifice and instruments inserted through one or more incisions in the skin, for example, in the abdominal area.

A surgical fastening assembly in accordance with the present invention comprises at least one elongate tubular body provided at a distal end with a sharp tip, at least one anchor disposed inside the elongate tubular body, an elongate push rod insertable into the elongate tubular body for advancing the at least one anchor by a distally directed motion of the push rod, and a coupling element operatively coupled to the at least one anchor for enabling the at least one anchor to be cinched to one or more additional anchors to thereby provide tissue approximation for securing of organic tissue. Preferably, but not necessarily, at least the one anchor comprises a plurality of wire elements or spines connected to one another. The anchor has an expanded use configuration, wherein the wire elements or spines are spaced from one another to facilitate grasping of tissue, and an insertion configuration in which the wire elements or spines are collapsed towards one another.

Pursuant to another feature of the invention, at least the one anchor is made at least partially of a spring biased metal or a shape memory alloy, which may display stress-induced martensite properties.

Pursuant to another feature of the invention, the wire elements or spines are concave on an outer side and convex on an inner side so that the wire elements or spines together define a splayed grappling hook shape, with tips of the wire elements or spines angled outwardly at a distal tip of the respective anchor.

Pursuant to a further feature of the invention, at least the one anchor is elastic and is configured to splay to an open state under a spring biased force upon ejection of the anchor from the tubular body. The wire elements or spines are preferably configured and operable to splay out when deployed into a target tissue. In addition, the wire elements or spines are preferably configured with sharply pointed curved distal ends.

The coupling element may take the form of a line element coupled to at least the one anchor.

Preferably, all of the anchors have the same structure and operation and are deployed in the same way.

The above described surgical fastening assembly may be deployed via an endoscope, i.e., inserted through a working channel of a flexible or rigid endoscope or through a sheath disposed around the endoscope insertion member. Alternatively, the surgical fastening assembly may be used as a separate instrument, for instance in a laparoscopic procedure, an interactive procedure whereby a flexible endoscope, and one or more laparoscopic instrument are utilized, or in open surgery.

A surgical fastening assembly in accordance with the present invention comprises a plurality of elongate tubular bodies connected to one another, the tubular bodies being provided each with a sharp tip at a distal end. Multiple anchors are disposed inside respective ones of the tubular bodies. Multiple elongate push rods are insertable into respective ones of the tubular bodies for advancing the anchors out of the tubular bodies by a distally directed motion of the push rods. At least one coupling element is operatively coupled to at least one of the anchors for enabling the anchors to be cinched together to thereby provide tissue approximation for securing of organic tissue.

Preferably, but not necessarily, the tubular bodies are being disposed substantially parallel to one another and disposed substantially parallel to one another.

Each of the anchors preferably comprises a plurality of wire elements or spines connected to one another. Each anchor has an expanded use configuration wherein the respective wire elements or spines are spaced from one another to facilitate grasping of tissue. Each anchor concomitantly has an insertion configuration in which the respective wire elements or spines are collapsed towards one another, the anchors being disposed in the insertion configuration inside the respective ones of the tubular bodies.

As indicated above, the anchors are made at least partially of a shape memory alloy, a shape memory alloy which displays stress-induced martensite properties, are temperature biased, a spring biased metal or other elastic material.

In accordance with another aspect of the present invention, the wire elements or spines of each one of the anchors are concave on an outer side and convex on an inner side so that the wire elements or spines of any given anchor together define a grappling hook shape, with tips of the wire elements or spines angled outwardly at a distal tip of the given anchor.

In accordance with additional features of the present invention, the tubular bodies are rigidly connected to one another and the push rods are rigidly connected to one another. Owing to the latter feature, all of the push rods may be advanced and the respective anchors ejected into or through target tissue simultaneously, with one motion of the operator.

A method for performing surgical operations on internal body tissues of a patient comprises, in accordance with the present invention, (i) pushing an elongate tubular body so that a distal end portion of the tubular body enters target tissue, (ii) thereafter ejecting a first anchor from the distal end of the tubular member, (iii) engaging the target tissue with the ejected anchor, (iv) retrieving a line element coupled with the anchor to an extracorporeal location, and (v) manipulating the line element outside of the patient to cinch the anchor to at least one other anchor engaging the target tissue, thereby approximating the target tissue.

In accordance with a further feature of the present invention, the method also comprises ejecting the one or more other anchors from a tubular member and thereafter engaging the target tissue with the one or more other anchors. The tubular member may be the same as or different from the tubular body (each a "tubular applicator"). In the former case, the anchors are deployed in seriatim. In the latter case, the anchors may be deployed simultaneously. In any case, the ejecting of the anchors from the respective tubular applicators is carried out subsequent to the pushing of the respective tubular applicators partially into or through the target tissue.

As indicated above, the tubular member and the tubular body may be connected to one another, a feature which facilitates the pushing of the tubular body and the pushing of the tubular member simultaneously.

Pursuant to an additional feature of the present invention, the method further comprises forming a perforation or incision in the target tissues prior to the pushing of the tubular body, the approximating of the target tissue serving to close the perforation or incision. The first anchor and the at least one other anchor engage the target tissues on different sides of the perforation or incision.

The perforation or incision so closed may be formed in a wall of a hollow internal organ of the patient, such as the stomach wall. In that case, the pushing of the tubular body may include inserting the distal end portion of the tubular body through the wall of the internal organ, the first anchor and the at least one other anchor engaging the wall along one side thereof (e.g., an outer side, facing into the abdominal cavity). The method may further comprise inserting the distal end portion of the tubular body though an external skin surface prior to inserting it through the wall of the internal organ. Such a procedure may be performed in interactive endoscopic surgery, comprising both endoscopic processes and procedures carried out through the abdominal wall. In that case, the method may additionally comprise inserting a distal end portion of an endoscope into the hollow organ. The forming of the perforation or incision may then be performed under visual observation afforded by the endoscope.

Concomitantly, a surgical method in accordance with the present invention comprises (a) inserting a distal end portion of a flexible endoscope insertion member into a hollow internal body organ of a patient via a natural body opening of the patient, (b) inserting a distal end portion of a surgical instrument into the internal body organ through a skin surface of the patient and a wall of the internal body organ, (c) actuating the surgical instrument from outside the patient to perform a surgical procedure at a surgical site inside the patient, and (d) operating the endoscope to view the surgical site during the actuating of the surgical instrument. The surgical site may be inside the hollow organ (e.g., the stomach) or external to the internal organ (e.g., in the abdominal cavity).

This method typically results in the formation of multiple artificial openings in organs of the patient. The method then further comprises closing at least one such opening in target tissue of the patient by (i) pushing an elongate tubular body so that a distal end portion of the tubular body enters target tissue, (ii) thereafter ejecting a first anchor from the distal end of the tubular member, (iii) engaging the target tissue with the ejected anchor, (iv) retrieving a line element coupled with the anchor to an extracorporeal location, and (v) manipulating the line element outside of the patient to cinch the anchor to at least one other anchor engaging the target tissue, thereby approximating the target tissue.

Where the surgical site is in the abdominal cavity of the patient outside the internal organ, the method further comprises passing the distal end portion of the surgical instrument through the wall of the internal organ into the abdominal cavity.

Thus, the anchoring system of the invention comprises an anchoring delivery and deployment assembly and related surgical anchors that may be used in conjunction with a flexible or rigid endoscope, or in isolation. The surgical anchors are coupled with suture thread or another line element to be used for approximating internal body tissues together through a synching operation.

In one embodiment, an endoscopic anchoring system as described herein comprises an elongate hollow or tubular body having an outer diameter sufficiently small, so as to be slidably insertable through a working channel of an endoscope. The hollow tubular body holds one or more anchors, and includes a pushing device or element to deploy the anchors, such as a rigid or flexible push rod that moves in the tubular body for pushing the anchors in the distal direction. The tubular body is provided at a distal end thereof with a sharp hollow tip, such as a hollow needle, which is coextensive with a distal end of the body and serves to pierce the target tissue for the purpose of delivering the anchors. The anchors have a collapsed state when positioned in the hollow tubular body and are operable to splay to an open state when ejected from the tubular body as further discussed herein below.

In another embodiment, the anchors include anchor spines, which are curved at their distal ends for anchoring into tissue, and are sharply pointed at their distal ends for the purpose of easily penetrating the tissue. Two corresponding spines are formed from one thin metal rod that is bent at a medial aspect thereof. Several such metal rods are thusly bent, and coupled with a crimping mechanism such as, for example, a metal ring or collar. The crimping mechanism is placed proximate the bight portion created by the bend in the rods, forming a proximal loop.

The distal spines extending from the crimping mechanism terminate with an outward curve as described above. When the spines are in their most open configuration, corresponding spines are situated at an angle of approximately 100 degrees from one another at the anchor's most splayed position, however function well even at lesser angels such as 70-80 degrees. An anchor may not be capable of opening to its maximal open position when embedded in tissue, therefore it is important that the anchor functions well even at a partially opened state. A suture thread or another line element traverses through the proximal loop of each anchor. While in the embodiment described above the loop is configured from the proximal bight portion of the spines held together by the crimping mechanism, in another embodiment the loop may be separately formed, as further described below.

The anchors are configured for engaging tissue and may be formed of a suitable material, such as metal or plastic, for example. In one embodiment the anchors are made of a shape memory alloy. Shape memory alloys (SMAs) are particularly useful for this application because of their ability to undergo a reversible transformation from an austenitic (hardened) state to a martensitic (malleable) state and vice versa with a change in temperature. This transformation is sometimes referred to as thermoplastic martensitic transformation.

In the embodiment wherein the anchors are made of an SMA, the spines are formed by "backing in" their open configuration. Thus, the desired configuration of the spines when in their hardened, austenite state is an open one, whereby the angles between spines are at about 110 degrees, and the distal aspects of the spines are at their maximum curve for optimal grasping, or anchoring into tissue.

These anchor spines rely on the property of shape memory to achieve their desired effect, that is to say, they rely on the fact that when the SMA spines are cooled to its martensitic (malleable) state, the anchor will be subsequently deformed and will retain its new shape, such as when stored inside the hollow tubular body, or the needle; but when it is warmed to its austenitic (hardened or firm) state, for example when released inside body tissue thereby being exposed to body temperature, the original shape (i.e., splayed in an open state) will be at least partially recovered, as discussed above.

In another embodiment, a crimping mechanism is used to hold the spines together, and may be formed of a different or similar material as the spines. The anchors are contained within the elongated tubular body that acts as an anchor delivery tube and terminates in a needle. The anchors are stacked behind each other inside the elongated tubular body, and are pushed forward by the pushing device that acts on the rearmost anchor's proximal end. As the rearmost anchor is pushed, in turn, it pushes the next anchor and so on until all of the anchors are deployed out of the distal end of the device.

Surgery for morbid obesity (bariatric surgery), which is being performed with much greater frequency, also requires either an open or laparoscopic technique. These patients are particularly risky to operate upon because of their co-morbidities, and the surgery takes hours with all the risks of prolonged anesthesia, and organ failure. A particular method of employing the anchoring device is described below, wherein a rather low risk endoscopic procedure is performed. This procedure results in a gastric restrictive operation, which may supplement, or precede the more invasive operation of intestinal bypass surgery.

A surgical method comprises, in accordance with the present invention, (a) inserting a distal end portion of a hollow needle into a hollow organ of a patient, (b) subsequently inserting the distal end portion of the needle through a portion of a wall of the hollow organ, (c) thereafter ejecting an anchor element from the distal end portion of the needle into the hollow organ, a flexible line element extending from the anchor element through the portion of the wall of the hollow organ to an extracorporeal location, (d) after the ejecting of the anchor, withdrawing the needle while retaining the anchor element and a distal end portion of the line element in the hollow organ, (e) inserting a distal end portion of an endoscope through a natural body opening into the hollow organ, (f) thereafter performing a surgical operation at least in part on the wall of the hollow organ at a point proximate to the portion of the wall of the hollow organ, and (g) after a completion of the operation, pulling the flexible line element from the extracorporeal location to cinch the wall of the hollow organ in a region including the point.

The inserting of the needle into the hollow organ may be accomplished through a skin surface of the patient, the flexible line element extending from the anchor out through the skin surface during the inserting of the distal end portion of the needle into the hollow organ and through the portion of the wall of the hollow organ. It is preferable that the distal end portion of the endoscope be inserted into the hollow organ prior to the inserting of the distal end portion of the needle. Thus, one may operate the endoscope to view the hollow organ from inside the same during the inserting of the distal end portion of the needle through the skin surface and into the hollow organ. The endoscope is also operated (from outside the patient) to view the hollow organ from inside the same during the inserting of the distal end portion of the needle through the portion of the wall of the hollow organ.

The needle may be inserted in seriatim, prior to the ejecting of the anchor, through multiple portions of the wall each proximate to the point of the operative procedure on the wall of the hollow organ.

The anchor may be a first anchor of a plurality of anchors used to cinch and close the wall of the hollow organ at the point of the operative procedure. In that case, the method additionally comprises (h) inserting the distal end portion of an additional needle into the hollow organ, after the withdrawing of the needle, and through at least one portion of the wall of the hollow organ, (i) thereafter ejecting a second anchor from the distal end portion of the additional needle and into the hollow organ, a second line element extending from the second anchor through the at least one portion of the wall of the hollow organ to the extracorporeal location, (j) thereafter withdrawing the additional needle from the hollow organ, and (k) after the completion of the operation, pulling the second flexible line element from the extracorporeal location to cinch the wall of the hollow organ in the region including the point.

The operation may include, for example, forming a perforation in the hollow organ at the point and passing the distal end portion of the endoscope through the perforation. Thus, the present invention provides a method for cinching closed a perforation in a hollow body organ during a normal-orifice translumenal endoscopic surgical procedure. The flexible line elements are manipulated extracorporeally at the end of the surgical procedure to cinch internal organs closed at desired locations.

BRIEF DESCRIPTION OF THE DRAWINGS

For purposes of clarity and brevity, like elements and components will bear the same designations and numbering throughout the Figures.

DETAILED DESCRIPTION OF EMBODIMENTS OF THE INVENTION

The surgical fastening assembly and associated closure method disclosed herein are useful in a variety of surgical procedures including endoscopic and laparoscopic operations and interactive endoscopic procedures involving both flexible endoscopes inserted through a natural body opening and instruments inserted through one or more incisions in the skin, for example, in the abdominal area. For use in an interactive endoscopic procedure, which combines flexible endoscopy with trans-abdominal access, the surgical fastening assembly and associated closure method are described herein with reference particularly to FIG. 15 et seq.

The term "endoscopic" is used herein to designate any of a variety of minimally invasive surgical procedures wherein optical elements are used to view internal spaces and tissues of a patient through relatively small surgically created openings or natural orifices. Concomitantly, the term "endoscope" as used herein refers to any optical or tubular instrument inserted through such openings or orifices for purposes of enabling visualization of and/or access to internal tissues during a minimally invasive procedure.

During a laparoscopic procedure, for example, an optical element may be inserted through one small incision, while one or more cannulas would be inserted through one or more separate incisions. The surgical instruments inserted through the cannulas are visualized by means of the first optical element. During a flexible endoscopic procedure on the other hand, a flexible endoscope may include, for example, both the optical element and one or more channels through which the surgical instruments are passed.

Figure 1:
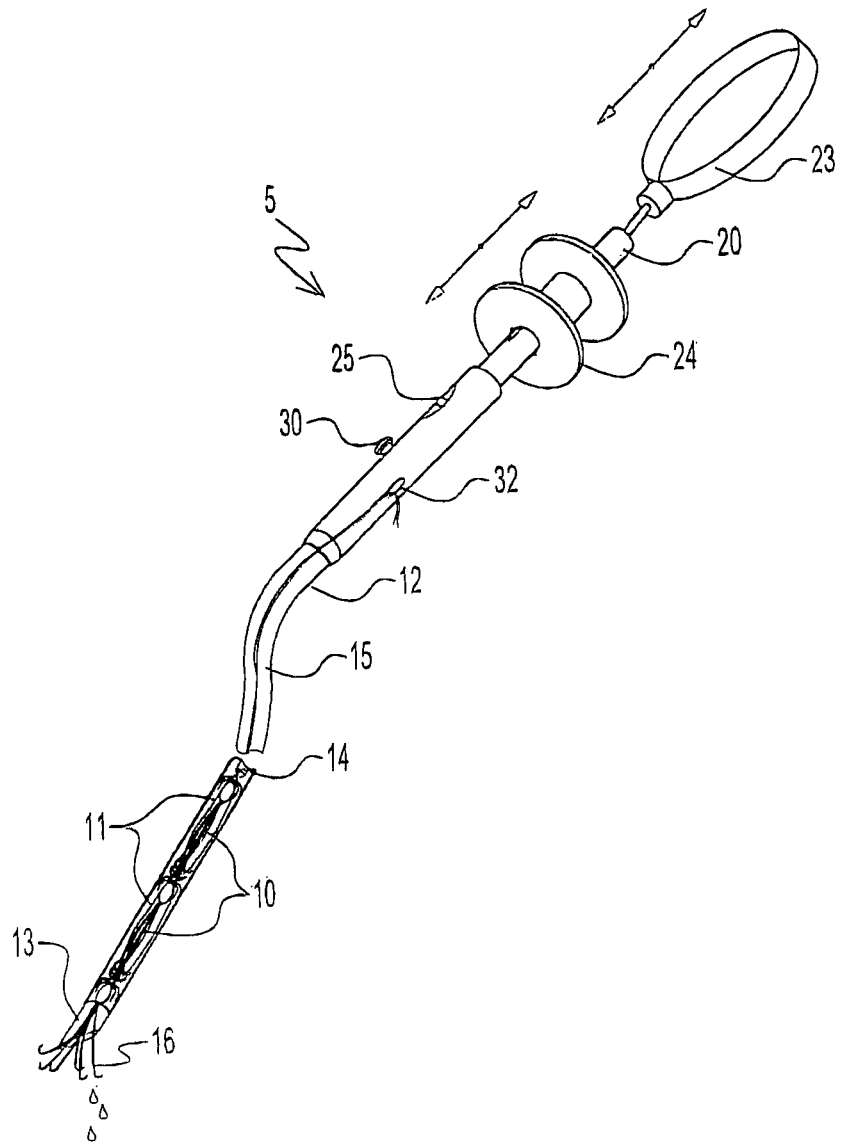
FIG. 1 is a perspective view of an endoscopic anchoring or closure assembly.

FIG. 1 is a perspective view of an endoscopic fastening assembly 5 in accordance with an embodiment of the invention. The fastening assembly 5 includes a plurality of anchors 10 attached to a thread or line element 11, and is configured to secure tissue that is internal to the body using a flexible or rigid endoscope. As such fastening assembly 5 is configured and operable to be manipulated within an endoscope during flexible endoscopy or a cannula during a laparoscopic procedure. Fastening assembly 5 includes an elongated hollow or tubular body 12 that holds a plurality of anchors 10 and an elongated pushing device to deploy the anchors, such as a pushing device 14 that moves or slides in body 12 for pushing anchors 10 distally for their deployment into tissue. The tubular body 12 is preferably flexible for being passed through and manipulated in a flexible endoscope, and terminates at said tubular body's distal end with a sharp hollow tip or hollow needle 13.

The anchors are configured for engaging tissue and may be formed of a suitable material, such as metal or plastic, for example. The anchors are preferably small enough to be deployed directly into the target tissue. In one example, the invention is used in the intestine and for that purpose the anchors must be small enough to be deployed into a patient's intestinal wall, which is approximately 0.5 cm thick.

In one embodiment, the anchors include fingers or spines and a crimping mechanism, wherein the spines are made of a shape memory alloy (SMA) such as Nitinol (NiTi). When the spines are formed from an SMA, they are deformed from their original "backed in" configuration, which is the open, splayed state of the anchor, to a new configuration such as a collapsed anchor state when cooled below the temperature at which the alloy is transformed from the austenitic to the martensitic state.

The temperature at which this transformation begins is usually referred to as Ms, and the temperature at which it finishes is Mf wherein M stands for martensite, s stands for start, and f stands for finish. When the spines thus deformed are warmed to a temperature at which the alloy starts to revert back to austenite, referred to as Af (Af being the temperature at which the reversion is complete), the deformed spines will begin to return to their original configuration, such as the splayed or open state.

In addition to the temperature dependence of SMA, certain shape memory alloys also display stress-induced martensite (SIM). When stress is applied to the alloy, it deforms elastically. At a critical stress, the austenitic alloy begins to transform to stress-induced martensite. This transformation takes place at essentially constant stress until the alloy becomes fully martensitic. From that point on, when further stress is applied, the martensite yields first elastically and then plastically.

When the stress is released, the martensite recovers elastically to a point at which there is zero residual stress, but a non-zero residual strain. Because the alloy is below As, the deformation is not recoverable until heating above As results in conversion to austenite. At that point, if the sample is unrestrained, or only minimally restrained such as the anchor inside tissue, the original shape baked into the anchor will prevail.

Certain Nitinol (NiTi) SMAs display stress-induced martensite at temperatures near mammalian body temperatures (35 to 40 degrees Celsius). For the invention, one can select any SMA, and test for the existence of the SIM effect at a desired temperature. In the example of one anchor embodiment made of the NiTi SMA, the SIM effect is displayed as follows: When the anchor 10 is stress stored inside the tubular body or needle 13, or even inside a stiffly flexible catheter or tubular body, it is in a stress induced martensite stage. When it is released while being embedded into tissue (body temperature being above As of the particular NiTi alloy, it transforms back into the austenite stage, with the anchor returning to its original splayed or open configuration, with hooked spines for optimal anchoring action in the target tissue.

One embodiment of an anchor includes a bullet or oval shaped body 34 that includes a plurality of wires or spines 16, which are coupled to the body. Alternatively, the anchor may be in the form of a plurality of wires or spines that are coupled together with a crimping mechanism 54. The anchor spines 16 are configured and operable to splay out to at least a partially open state when deployed into a target tissue.

Figure 6:
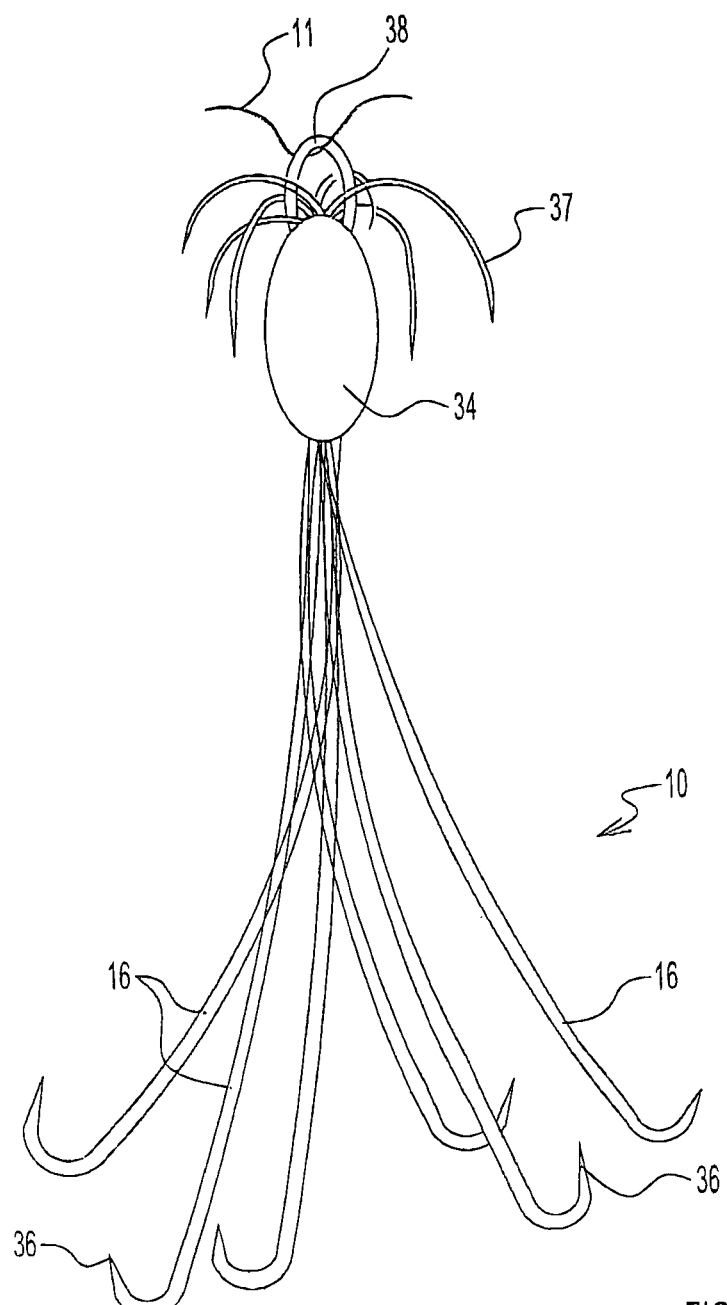
FIG. 6 is a perspective view of a full open anchor in accordance with the present invention.
Figure 7:
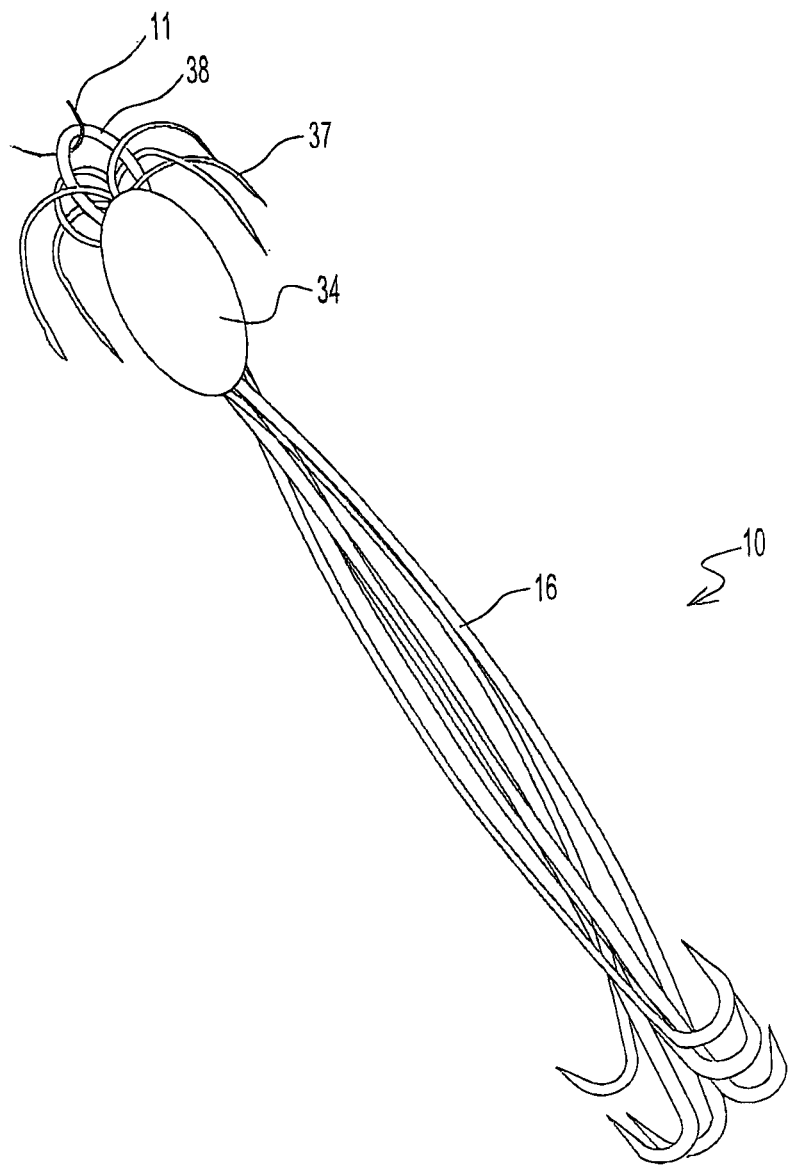
FIG. 7 is a perspective view of an anchor as in FIG. 6 in a collapsed state and held together by a crimping mechanism.

The spines 16 include curved and sharp distal ends 36 for grasping tissue and preventing migration of the anchor in the tissue as shown in FIGS. 6 and 7. In one embodiment, the spines 16 might also include curved proximal ends 37 for further grasping tissue (FIGS. 6 and 7). In another embodiment, the anchor is elastic and is configured to splay to an open state under a spring bias force. For example, the anchor spines may be stainless steel.

Whether the spines are made of a shape memory alloy or an elastic spring bias material, the anchor body or crimping mechanism may be made of the same or different material as the spines.

Figure 2:
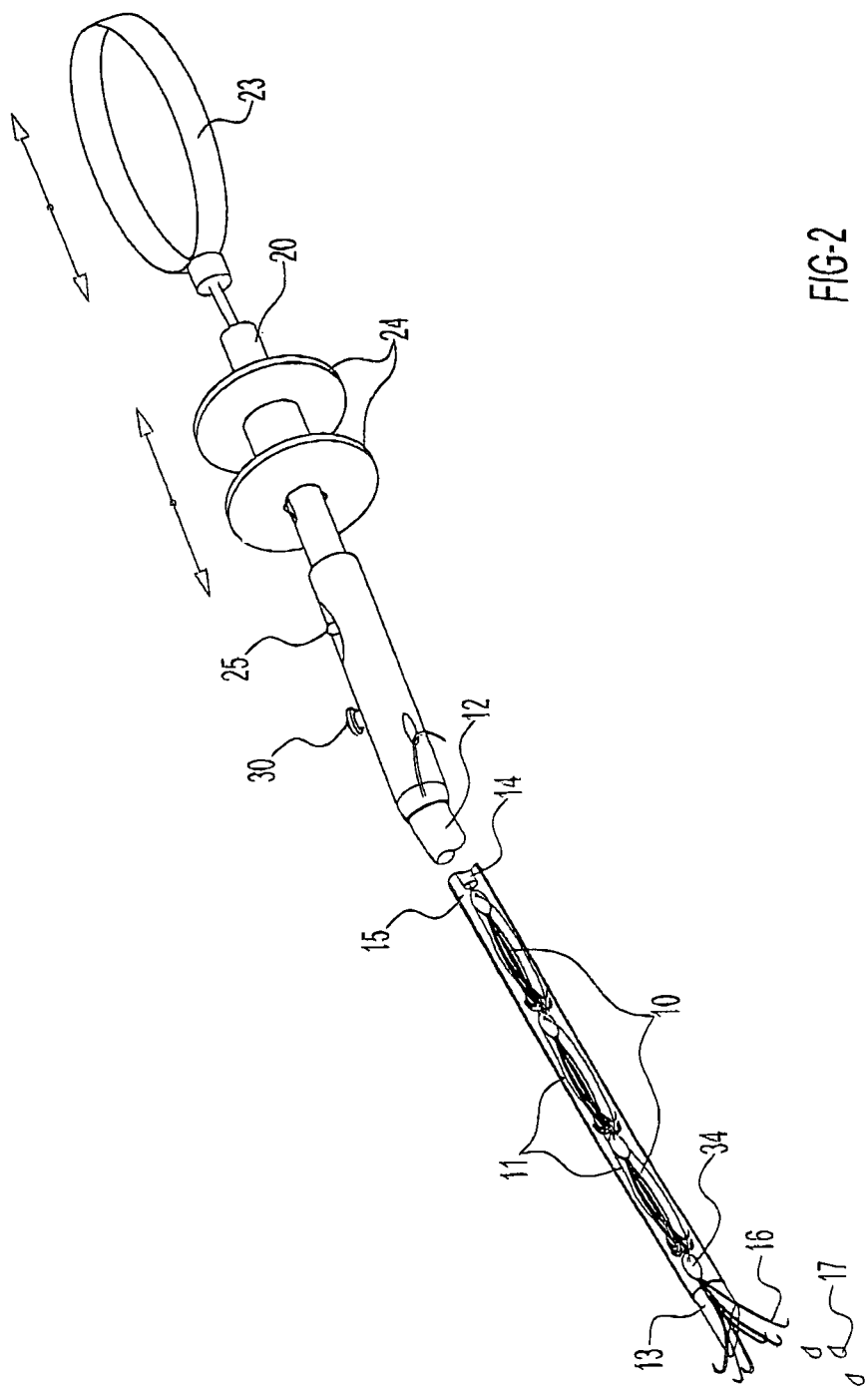
FIG. 2 is another perspective view of another endoscopic anchoring or closure assembly.

Tubular body 12 terminates in a sharp tip or hollow needle 13 configured to pierce and enter a target tissue as shown in FIGS. 1 and 2. The anchors are deployed out of the end of needle 13.

The expandable anchors 10 are contained in a collapsed state within tubular body or catheter 12. In one embodiment, body 12 includes a fluid passageway 15 to conduct hot fluid to induce an austenitic state, namely the splaying of the spines and the curvature of the individual spines 16 of the anchors 10. The same embodiment may be used to conduct cold fluid to induce the malleable, martensitic state if necessary.

The assembly 5 includes an actuation mechanism or handle 20 that is provided with a thumb ring 23 and finger ring 24, used to move the pushing device 14 for the purpose of deploying anchors 10. Actuation mechanism 20 includes an indexing locking mechanism 25 for positive stops of the push rod and for individual deployment of each anchor.

Figure 4:
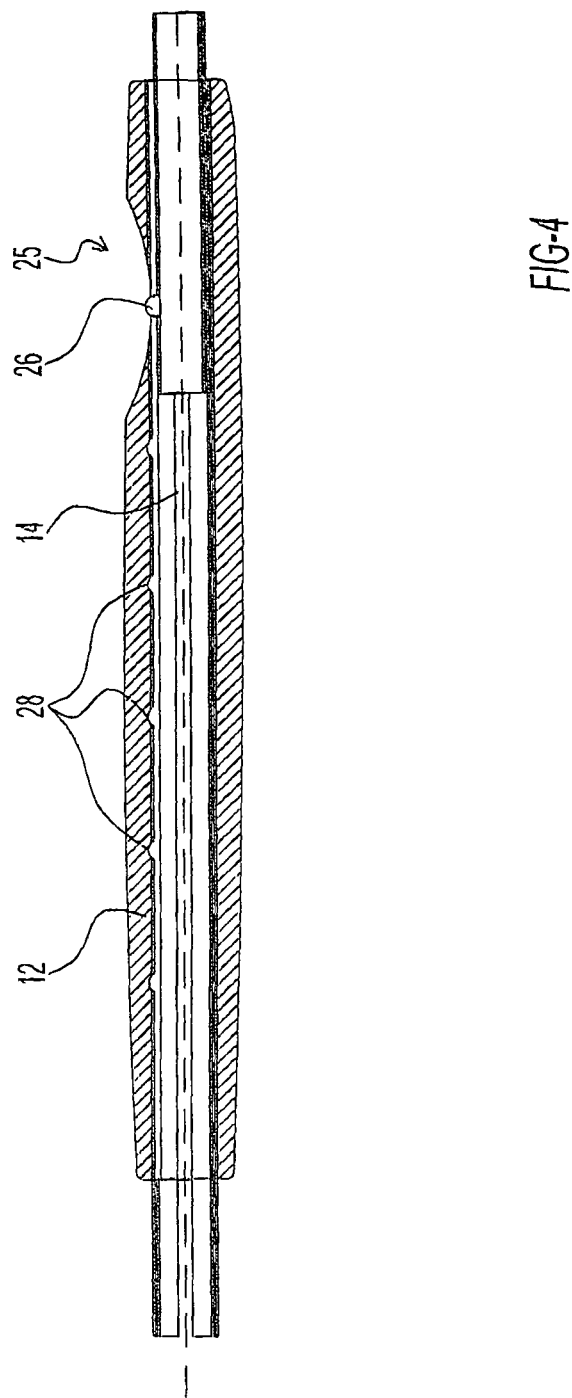
FIG. 4 is a cross sectional view of a portion of an endoscopic anchoring or closure assembly, showing a locking mechanism.
Figure 5:
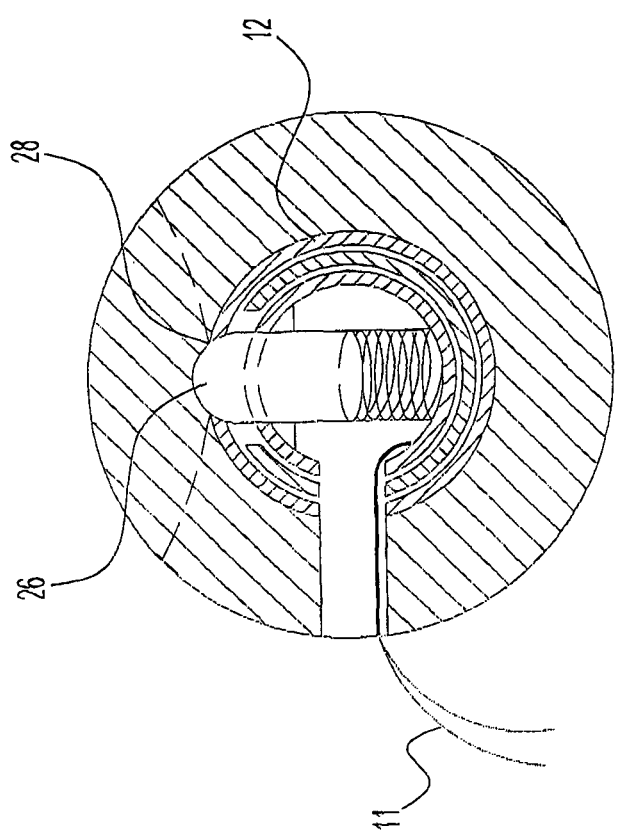
FIG. 5 is a cross sectional view of the portion of FIG. 4 showing a ball catch of the locking mechanism.

FIG. 4 illustrates an embodiment of the locking mechanism for pushing device 14 wherein a spring-loaded ball catch 26 (see FIG. 5) engages a series of indents 28 formed in elongated hollow tubular body 12. Device 5 also includes a fluid injection port 30 for introducing fluid 17 toward the passageway 15 and a thread-port 32 for introducing thread, or line element 11. FIG. 2 shows another perspective of device 5.

Referring to FIG. 2, the cutaway sectional view of the distal end of device 15 illustrates anchor spines 16 emerging from the end of the elongated body 12 and splaying out to an open configuration for anchoring tissue. As illustrated in FIG. 6, the spines 16 have sharp, curved ends 36, for respectively piercing, penetrating and anchoring tissue as noted below. A crimping mechanism 34 forms a body that holds the individual spines 16 together.

Figure 14:
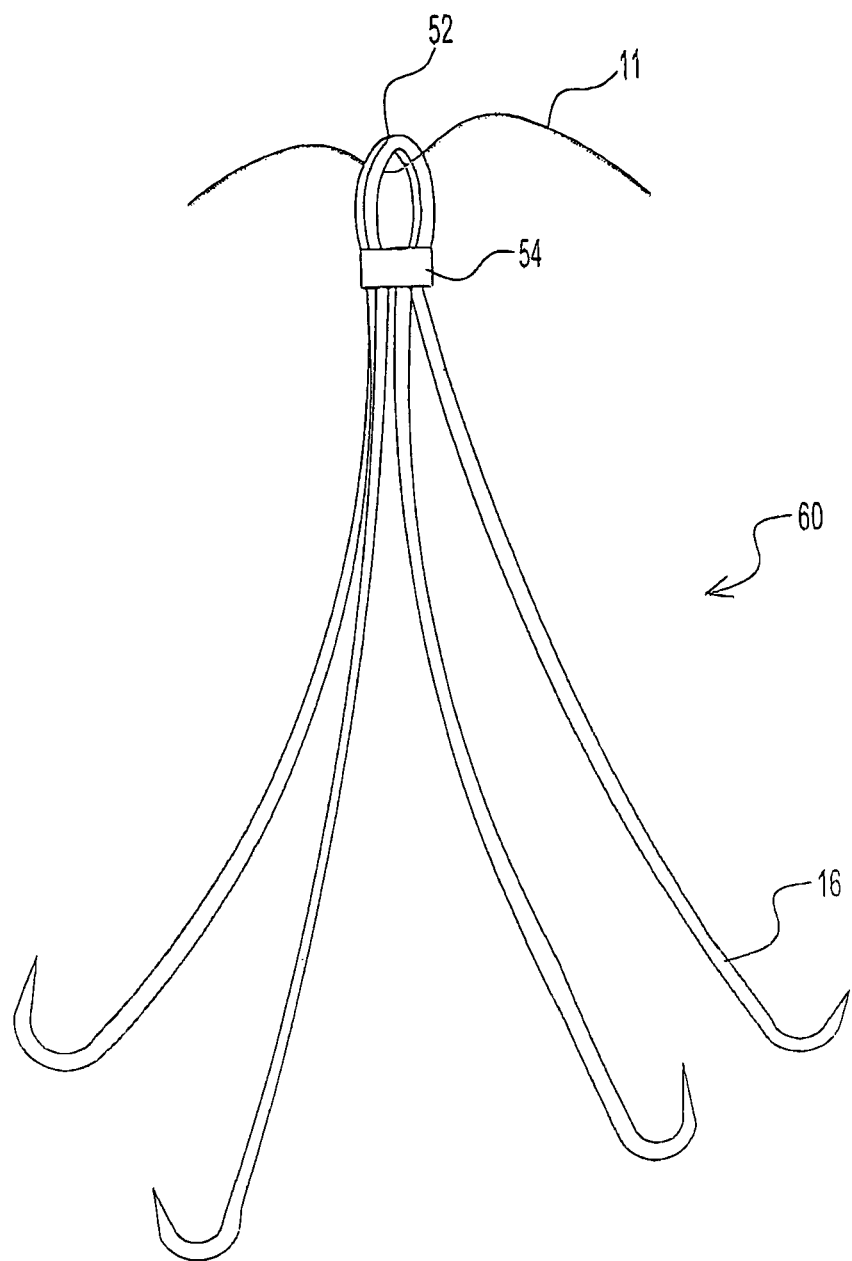
FIG. 14 is a perspective view of another embodiment of an anchor in an open configuration.

The crimping mechanism is also illustrated in FIG. 14. In this embodiment of the present invention, crimping mechanism 54 constitutes a metal ring or collar that-tightly encircles sections of the spines. For example, the spines may be formed from elongated elements having a curved and pointed end at both ends. The elongated elements can then be bent, approximately midway along the element to form multiple spines. A crimping mechanism 54 holds the spines together below the bend to effectively form a loop 52 through which a line element, such as a suture thread, may pass to hold the anchors together.

Returning to FIG. 6, a line element or thread 11 runs through a proximal loop 38 of anchor 10. The crimping mechanism 34, which acts as a body for the anchors 10, may be formed of a different or similar material as spines 16. Rather than loop 38, the body 34 might be provided with an opening through which line element 11 may traverse.

The anchors 10 are contained within the elongated body 12, which in certain embodiments is configured for holding a plurality of anchors. The anchors 10 are stacked behind one another inside elongated tubular body 12. Anchors 10 are pushed forward by pushing device 14, the distal end thereof is proximate the proximal end of the most proximal anchor. Thus, as the rearmost anchor is pushed, it in turn pushes the next anchor and so on until all of the anchors are deployed from the distal end of the device 5.

The spines 16 of FIGS. 6 and 7 are dual ended spines 16 being held together by crimping mechanism 34. The suture thread 11 runs through a loop 38 in the distal end of the anchor 10. In one embodiment, the anchor spines are made of a shape memory alloy. The spines might assume a martensitic state when forcibly collapsed, so as to be collapsed and passed through elongated body 12 and a flexible endoscope. The spines assume an austenitic state transforming the anchor into a certain splayed or spread configuration at body temperature when positioned inside a target tissue. The curvature of the curved ends 36 and/or 37 might also be affected by body temperature rendering the ends stiffer and more curved for providing optimal anchoring.

While body temperature is one way to achieve an austenitic state with an anchor made from an SMA, an alternative embodiment might deliver warm fluid to the anchors through fluid port 30 and passageway 15 to induce an austenitic state.

FIG. 7 illustrates a fully retracted or collapsed anchor 10 with dual ended spines 16 held together by crimping mechanism 34. This is generally the configuration in which the multiple anchors would be stored in elongated tubular body 12 of fastening assembly 5 prior to being deployed.

Figure 1A:
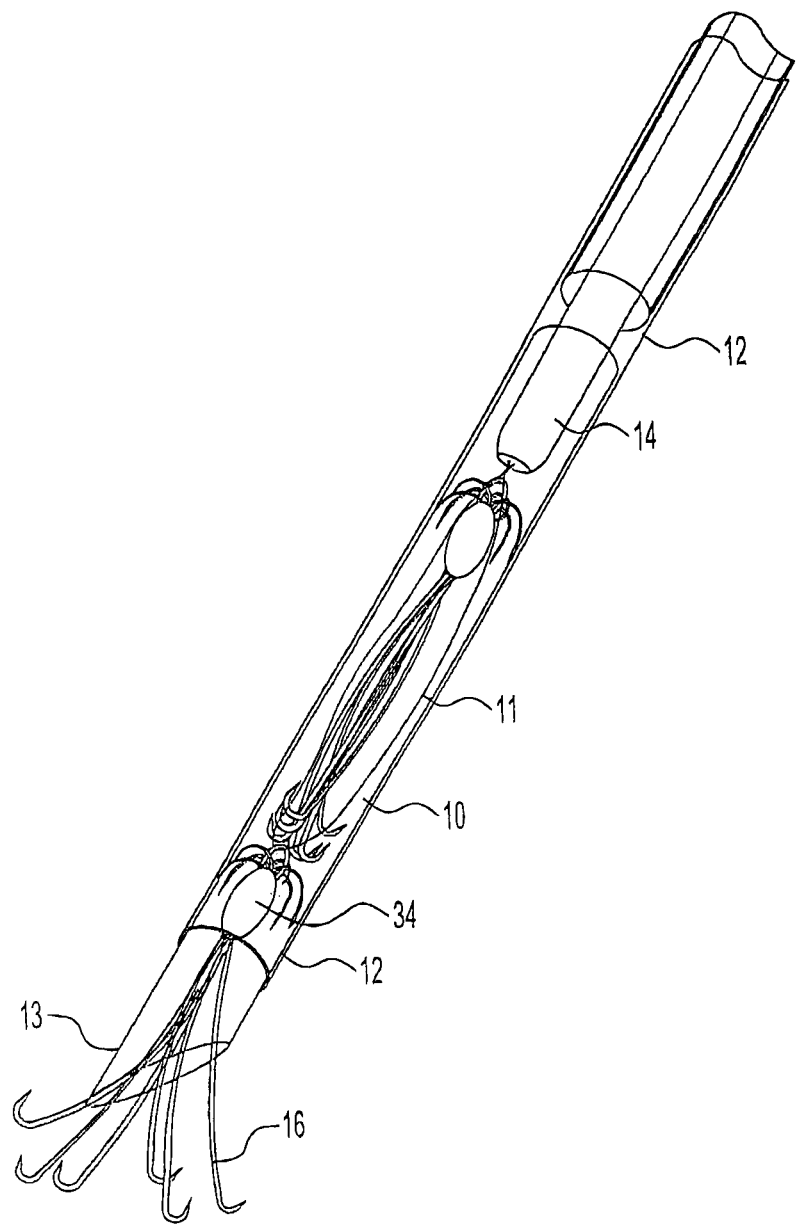
FIG. 1A is a perspective view of the distal end of the assembly of FIG. 1.
Figure 8:
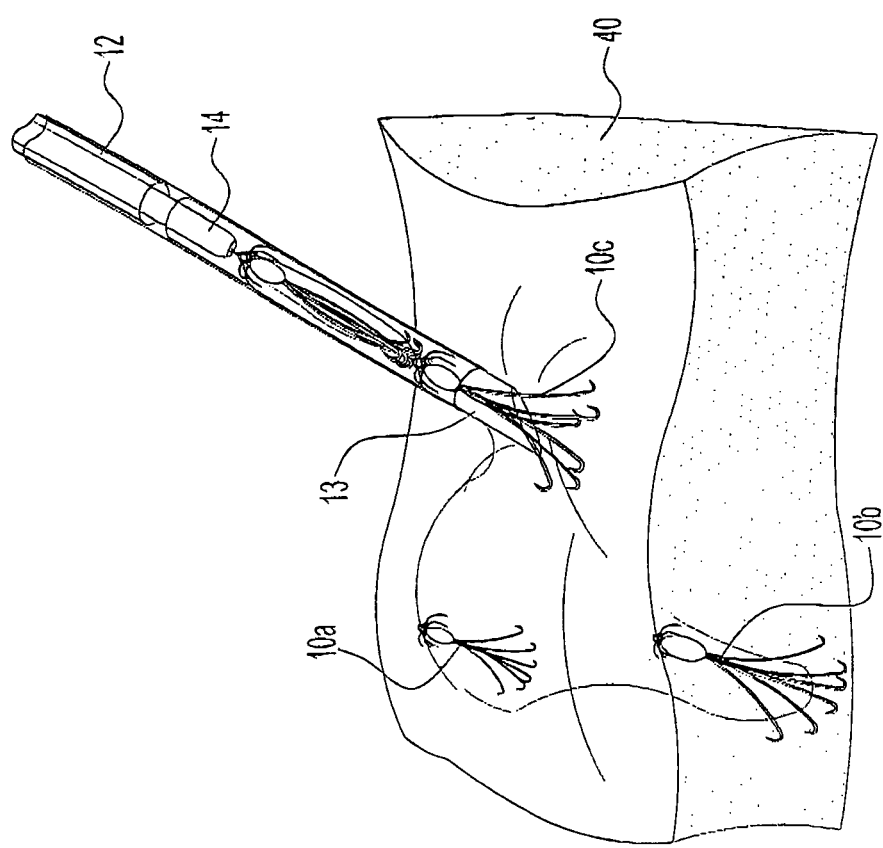
FIG. 8 is a perspective view of the anchors being deployed into tissue in accordance with the present invention.

FIG. 8 illustrates the fastening assembly 5 with a plurality of anchors 10 being deployed into tissue 40 through hollow needle 13 and coupled by a suture thread or other line element. As illustrated, anchors 10a and 10b have been deployed and anchor 10c is being deployed. Anchors 10 emerge from needle 13 being pushed by pushing device 14. The needle may be elongated as shown in FIG. 1A to form an anchor holder within elongated tubular body 12. Alternatively, there may be another anchor holder mechanism employed in tubular body 12, serving to hold the anchors inside tubular body 12 until they are deployed. The anchors 10 are stacked in needle 13 or other anchor holder as shown in FIGS. 1, 1A and 2 so that the anchors will be deployed sequentially, one at a time, with the anchors being pushed by the next sequential anchor or by pushing device 14.

Figure 3:
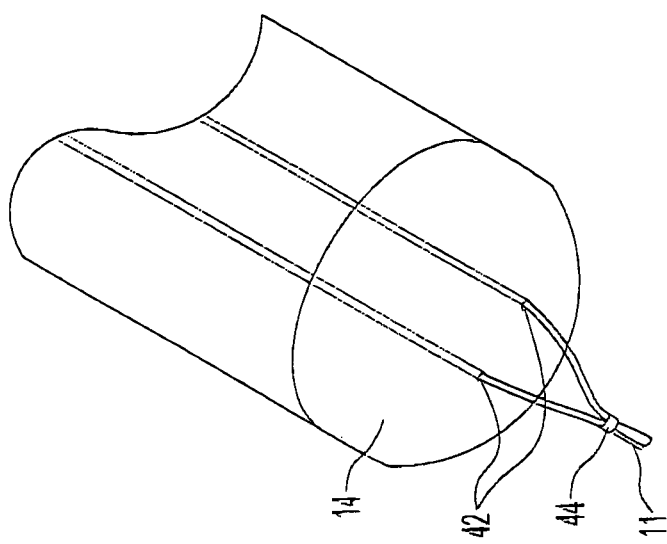
FIG. 3 is a perspective view, cut away, of a pushing device utilizable in the endoscopic anchoring or closure assembly of FIG. 1 or FIG. 2.
Figure 9:
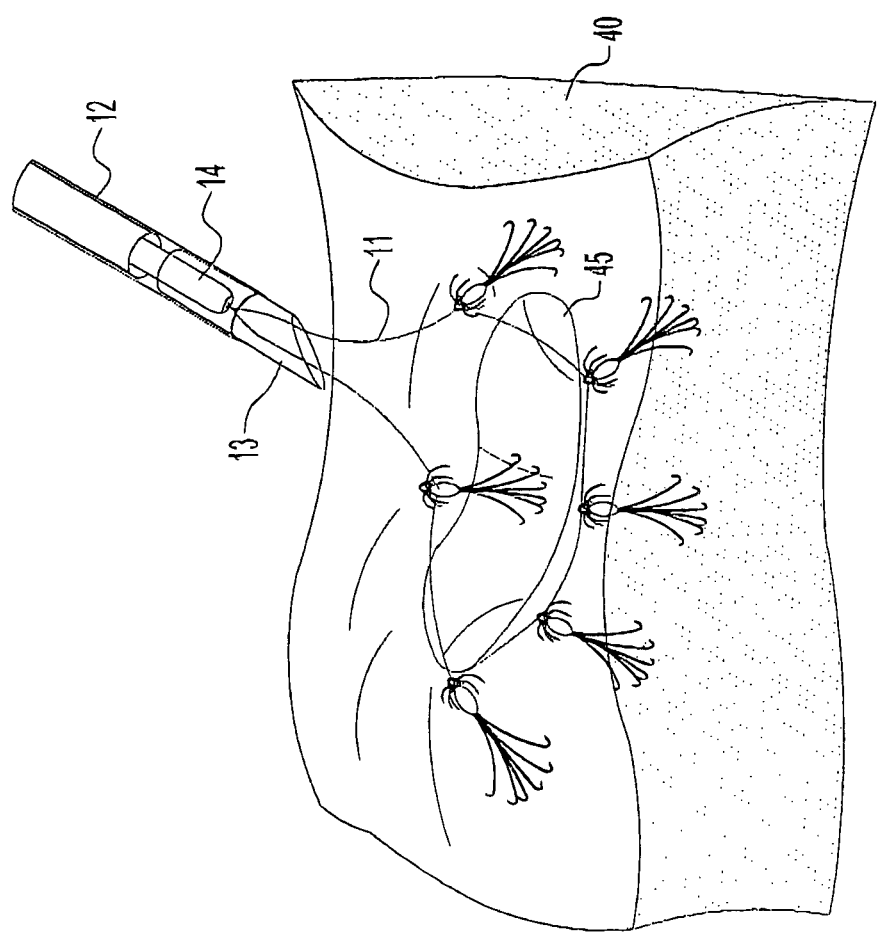
FIG. 9 is a perspective view of the anchors of FIG. 8 deployed in tissue and connected by a line element in the form of a purse string.

FIG. 9 shows anchors 10 deployed in tissue 40 and connected by thread or line element 11, with thread 11 traversing longitudinally through the center of push rod 14. Thread 11 may be a suitable wire or suture. Referring to FIG. 3, thread 11 may be fed through openings 42 in rod 14. The thread may be secured at one or more places along its length with a clip or collar 44.

Anchors 10 are shown positioned in tissue 40 to surround an opening or incision 45 in the tissue so as to close the incision. Thread 11 is flexible and biocompatible, and may be made of a bioabsorbable or non-bioabsorbable material. Furthermore, the thread may come in various thicknesses. Anchors 10 are coupled together with thread 11 in such a fashion as to facilitate cinching or pulling together of the deployed anchors causing a cinching or pleating of the target tissue. Once anchors 10 are positioned in tissue 40 as shown in FIGS. 8 and 9, the thread may be used to cinch the anchors for approximating segments of tissue together. The thread or line element might be continuous or common to couple all anchors together or each anchor may have its own line element, such that when cinching together is desired, all line elements are coupled together.

Figure 10:
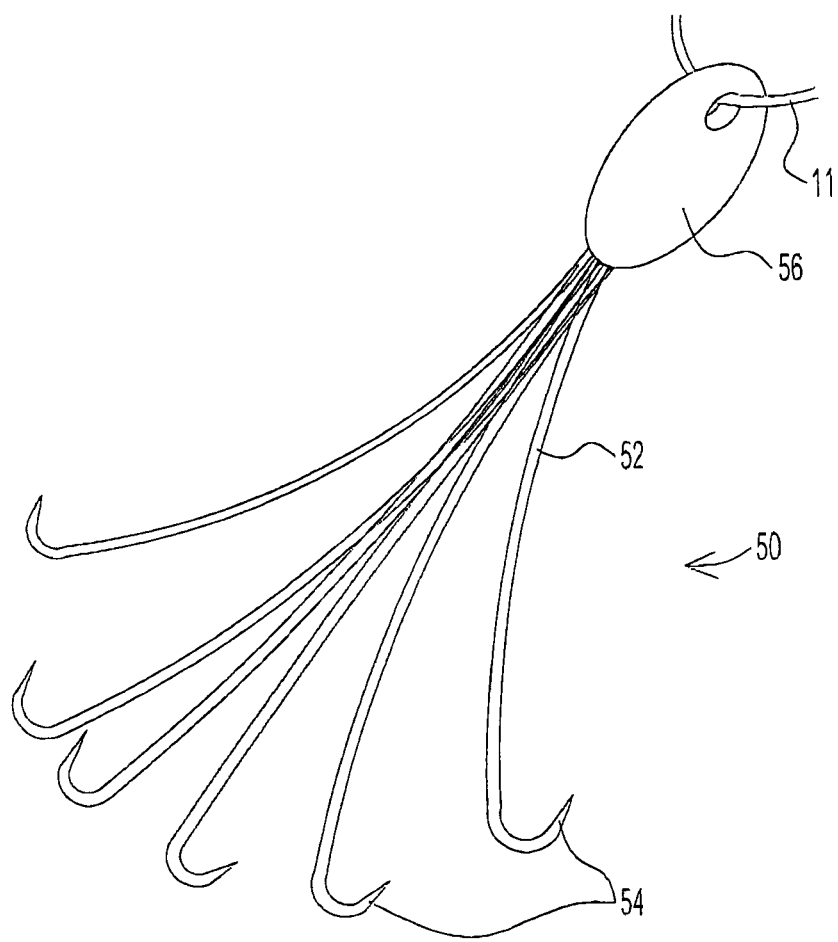
FIG. 10 is a perspective view of a full open alternative anchor.

FIG. 10 is a perspective view of an alternative anchor 50 of the invention in an open configuration. Anchor 50 includes spines 52 that have hooks or curved ends 54 only at the spines' distal ends. The spines are held together by crimping mechanism 56 and suture thread 11 traverses an opening formed in the crimping mechanism. Crimping mechanism 56, which acts as a body for anchor 50, may be formed of a different or similar material as spines 52.

Figure 11:
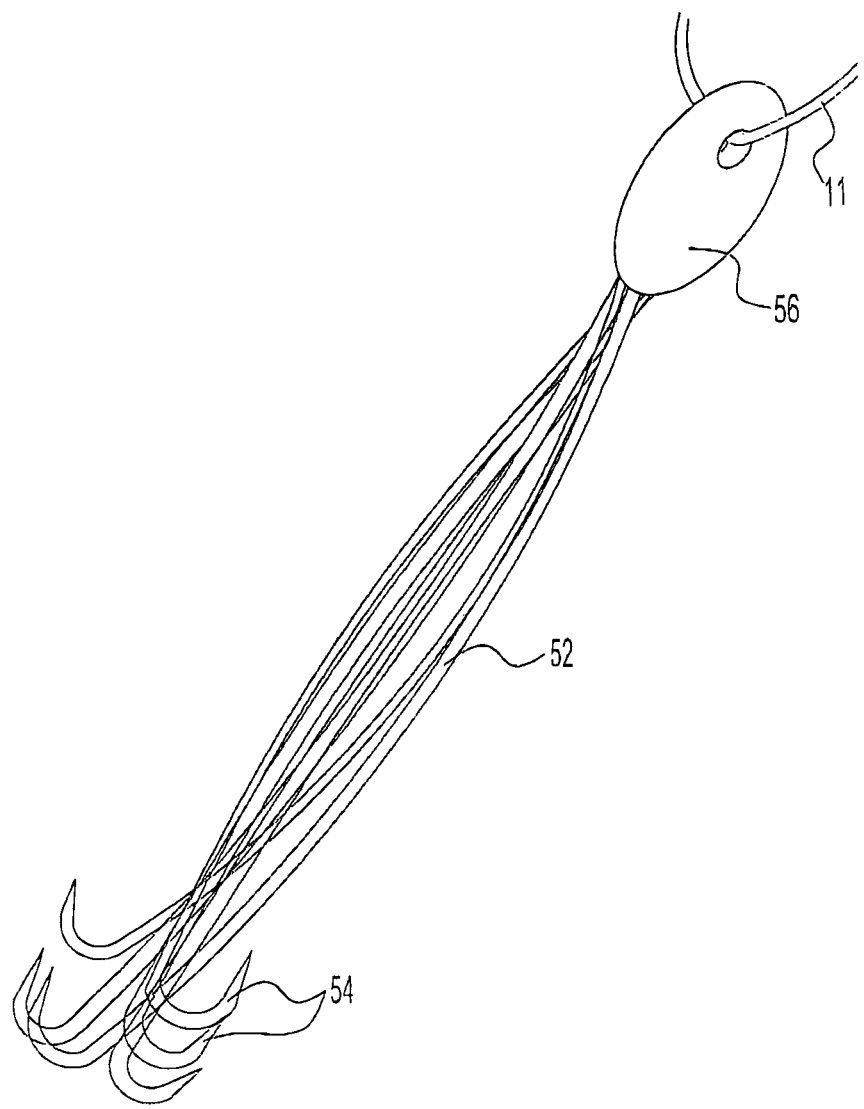
FIG. 11 is a perspective view of an anchor as in FIG. 10 in a collapsed state.

FIG. 11 shows a fully retracted anchor 50 with spines 52 in a collapsed state and held together by crimping mechanism 56.

Figure 12:
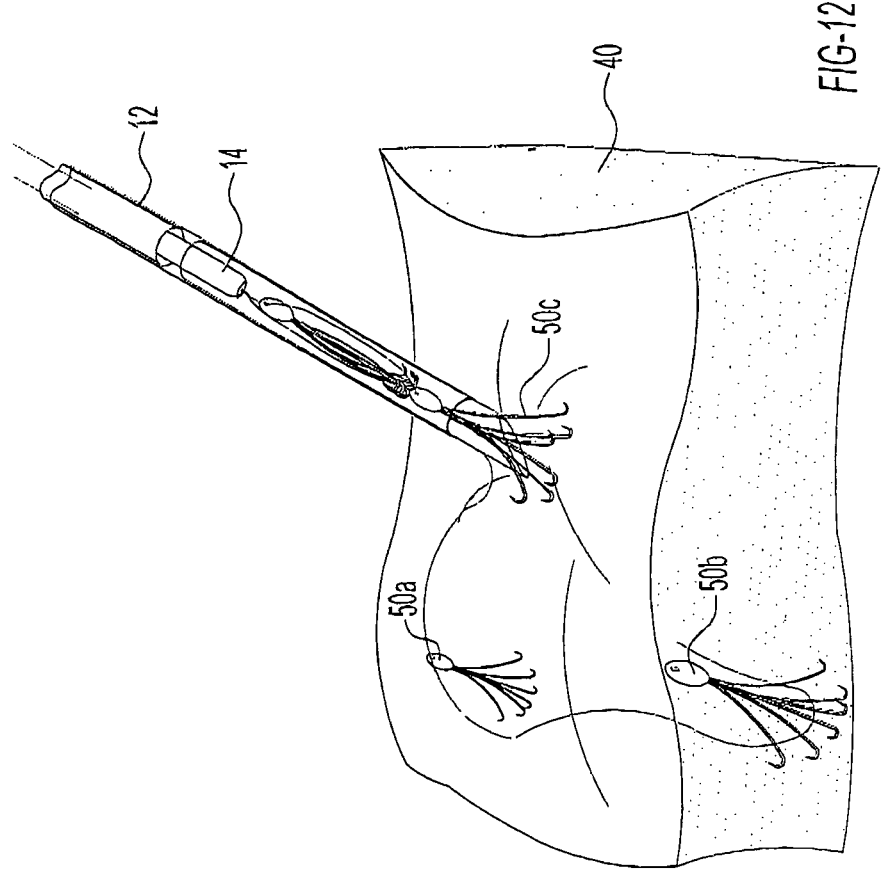
FIG. 12 is a perspective view of anchors being deployed into tissue.

FIG. 12 illustrates device 5 in use in tissue with a plurality of anchors 50 being deployed into tissue 40 through hollow needle 13 and connected by thread 11. For example, anchors 50a and 50b have been deployed and anchor 50c is in the process of being deployed inside tissue 40. Anchors 50 emerge from needle 13 with pushing device 14 pushing anchors 50 contained in elongated body 12. The needle may be elongated as shown in FIG. 1A to form an anchor holder within body 12. If the device is to be used in conjunction with a flexible endoscope, the needle must be 1.5 centimeters or shorter, because the maximal stiff length that can pass through a flexible endoscope cannot be longer than 1.5 centimeters.

Figure 13:
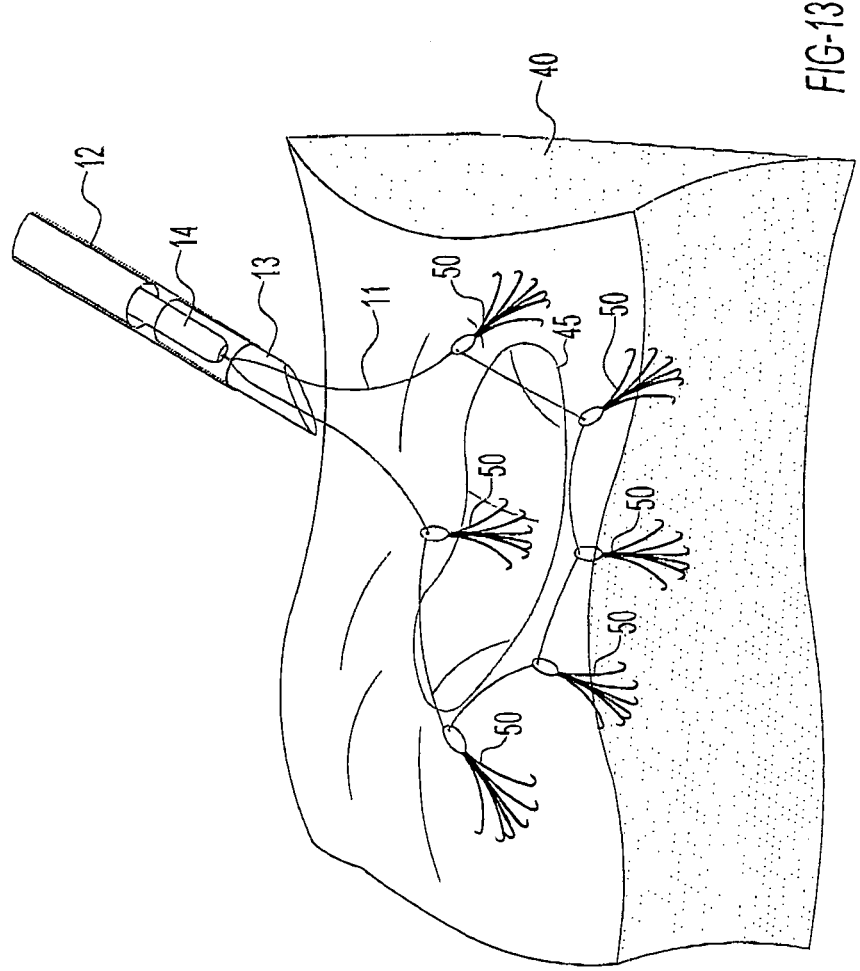
FIG. 13 is a perspective view of the anchors of FIG. 12 deployed in tissue and connected by a line element.

FIG. 13 illustrates anchors 50 deployed in tissue 40 and connected by a line element, such as a suture, thread 11 or wire, with line element or thread 11 running through the center of pushing device 14. Referring again to FIG. 3, thread 11 may be fed through openings 42 in pushing device 14. Thread 11 may be secured at one or more places along its length with a device such as a clip or collar 44.

Using the present invention, certain bariatric procedures might be performed. A flexible endoscope might be inserted through the mouth, and esophagus into the stomach. The cinching, pleating or approximating of tissue using fastening assembly 5 and anchors 10 may be accomplished by pulling on embedded anchors 10 to thereby restrict the volume of the stomach or make for an effectively smaller entryway into the stomach. Alternatively, an anti reflux procedure might be performed. The cinching, pleating, or approximating of tissue using the device by pulling on the coupling suture thread that communicates between the anchors that are embedded below an incompetent gastroesophageal sphincter restricts the opening of the sphincter, thus treating gastroesophageal reflux disease (GERD).

In another aspect of the invention, a method of performing any sphincter tightening or reduction might be deployed. Cinching, pleating or approximating of tissue by pulling anchors that are embedded at or near a sphincter constricts the lax sphincter. Fastening assembly 5 might also be used for suturing, control of hemorrhage or closing a perforation by delivering two or more anchors at opposite sides of a bleeding or perforation site, and cinching the anchors together.

Figure 15:
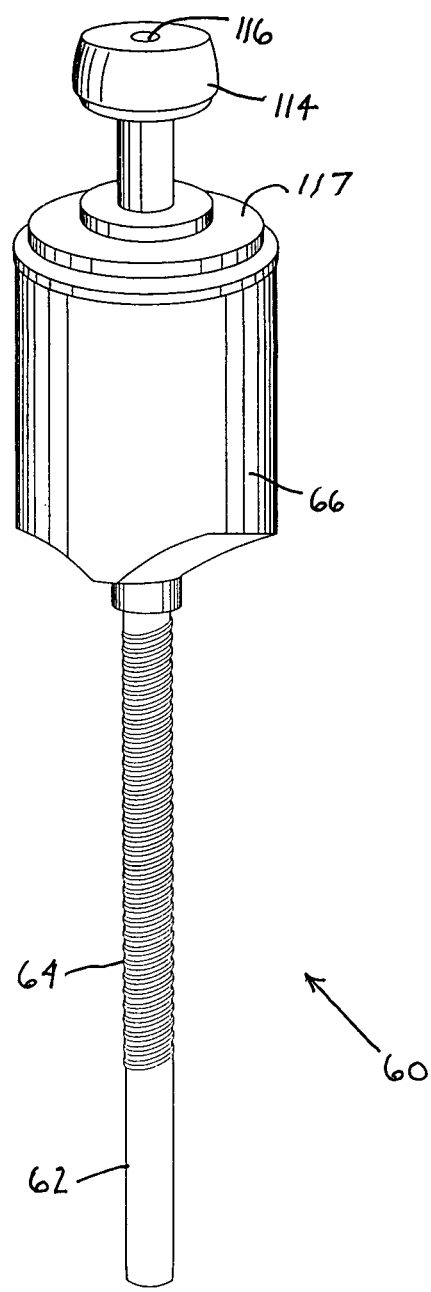
FIG. 15 is a perspective view of a laparoscopic cannula.

FIG. 15 shows a laparoscopic-type cannula 60 utilizable in an interactive endoscopic procedure, which combines flexible endoscopy with trans-abdominal access. In such a procedure, a flexible endoscope insertion member is inserted into a hollow organ such as the stomach through a natural body opening such as the mouth, while one or more elongate instrument shafts are inserted into the hollow organ through a skin surface such as in the abdominal area. These trans-abdominal instruments are operated from outside the patient under visual observation afforded by the endoscope. A surgical procedure may be performed in the hollow organ or on another organ. In the latter case, the distal ends of the endoscope and the trans-abdominal instruments are passed through incisions or perforation made in the wall of the hollow organ. At the end of the procedure, the instruments are withdrawn. The incisions or perforations are closed by means of a surgical fastening assembly as discussed below with reference to FIG. 15 et seq.

Figure 16:
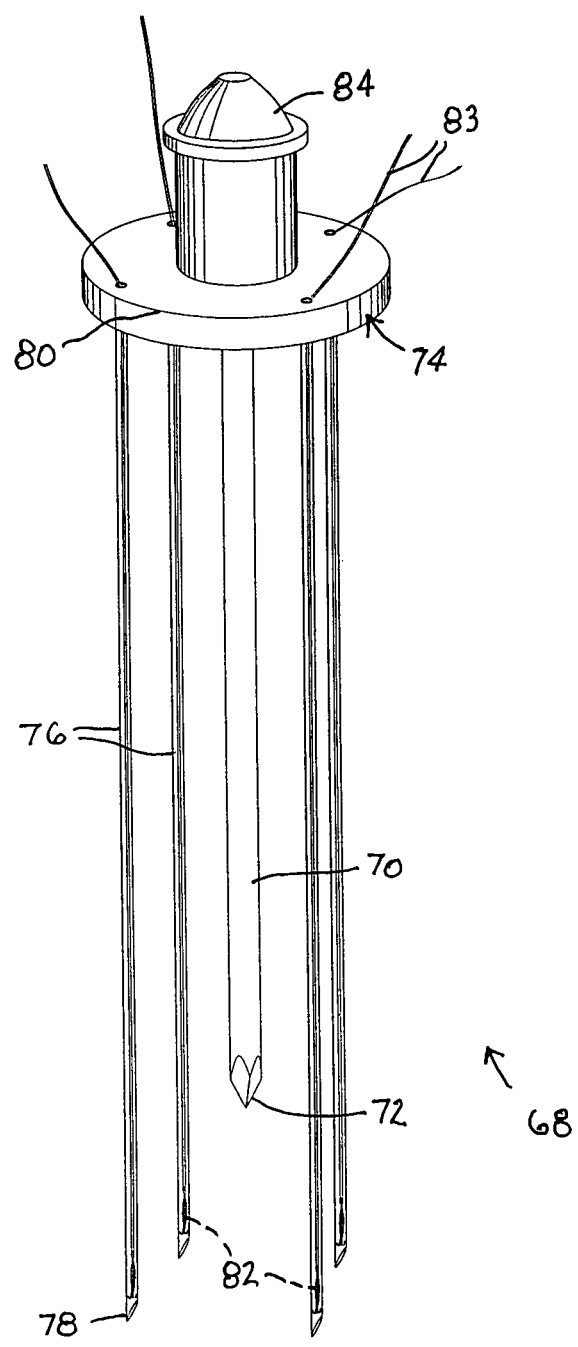
FIG. 16 is a perspective view of a multiple-fastener delivery assembly with an integrated trocar, in accordance with the present invention.

Cannula 60 comprises an elongate tubular member 62 which may be provided along at least a portion of its length with an external worm thread 64 or other protuberances for facilitating temporary retention in the abdominal wall of a patient. Cannula 60 further comprises an exterior cylinder 66 of enlarged diameter to serve as in part as a seat for a fastener delivery device 68 shown in FIG. 16.

Delivery device 68 includes a trocar 70 provided at a distal end with a sharp tip 72 and rigid at a proximal end with a holder disk or plate 74. Delivery device 68 further comprises a plurality of elongate tubular bodies 76 each provided at a distal end with a sharp tip 78 and rigid at a proximal end with plate 74. Tubular bodies 76 take the form of hollow needles that are angularly equispaced about the perimeter or edge 80 of plate 74. Tubular bodies 76 serve as deployment tubes for delivering respective multiple-spine anchors 82 to a surgical closure site inside a patient. At the onset of a surgical closure procedure using delivery device 68, anchors 82 are disposed in a collapsed configuration inside the distal ends of deployment tubes 76, with line elements or suture threads 83 each attached at one end to a respective anchor 82 extending out of proximal ends of deployment tubes 76. Suture threads 83 are coupling elements attached respective anchors 82 for enabling the anchors to be cinched together to thereby provide tissue approximation for securing of organic tissue. Delivery device 68 further includes a handle 84 disposed on a side of disk or plate 74 opposite deployment tubes 76 and trocar 70.

As discussed above with respect to endoscopic embodiments of a fastening delivery device, anchors 82 are made at least partially of a spring biased metal or a shape memory alloy, which may display stress-induced martensite properties. Anchors 82 have wire elements or spines 82a that are concave on an outer side and convex on an inner side so that the wire elements or spines together define a splayed grappling hook shape, with tips of the wire elements or spines angled outwardly at a distal tip of the respective anchor.

Anchors 82 may be elastic and configured to splay to an open use configuration under a spring biased force upon ejection of the anchors from the respective tubular deployment tubes 76. Wire elements or spines 82a are preferably configured and operable to splay out when deployed into a target tissue. In addition, the wire elements or spines are preferably configured with sharply pointed curved distal ends.

Figure 17:
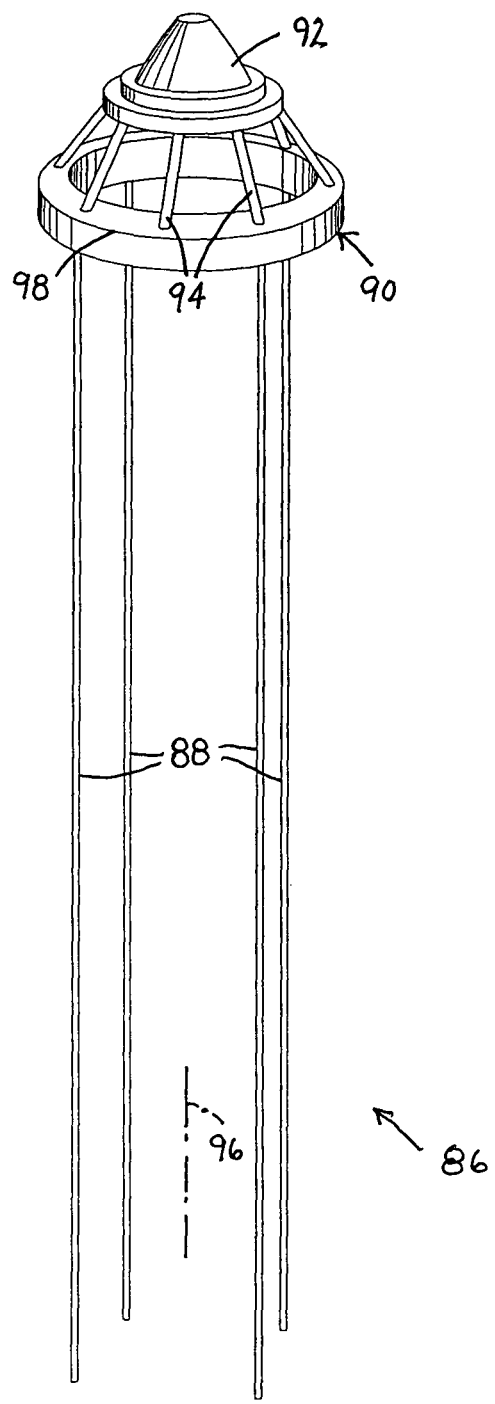
FIG. 17 is a perspective view of a pusher device utilizable with the multiple fastener delivery assembly of FIG. 16, pursuant to an embodiment of the present invention.

FIG. 17 depicts a pusher device 86 that is utilizable with delivery device 68 to deploy anchors 82 at a target surgical site. Pusher device 86 includes a plurality of elongate push rods 88 each connected at a proximal end to a holder ring 90. On a proximal side of ring 90, opposite rods 88, is a handle 92 connected to ring 88 by a number of radiating struts 94. Struts 94 are inclined at an angle relative to a longitudinal axis 96 of the pusher device 86. Rods 88 are angularly equispaced about a perimeter or edge 98 of ring 90 at locations that permit an insertion of the rods into respective deployment tubes 76 of delivery device 68.

Figure 18:
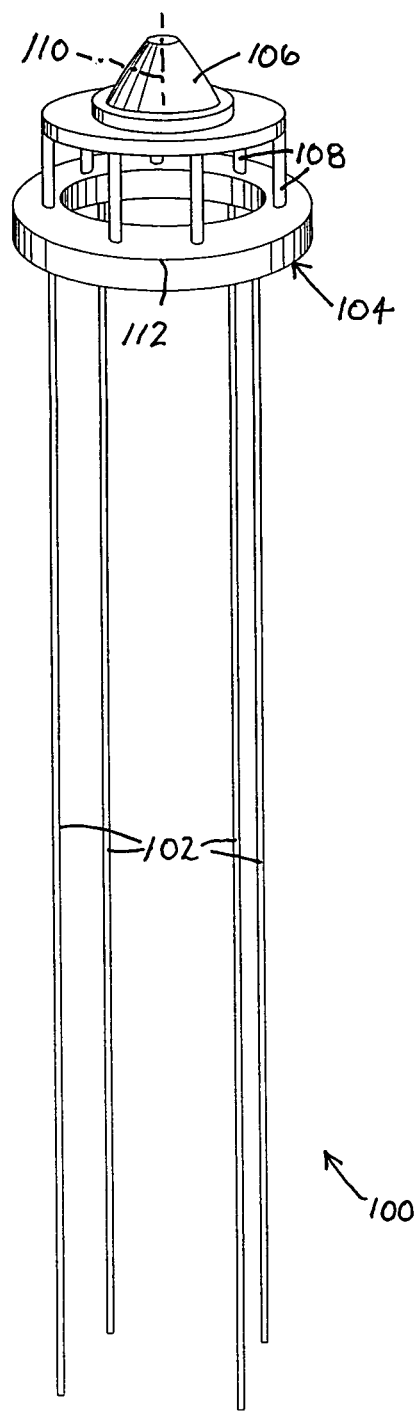
FIG. 18 is a perspective view of a modification of the pusher device of FIG. 17.

FIG. 18 depicts a modified pusher device 100 also utilizable with delivery device 68 to deploy anchors 82 at a target surgical site. Pusher device 100 includes a plurality of elongate push rods 102 each connected at a proximal end to a holder ring 104. On a proximal side of ring 104, opposite rods 102, is a handle or end cap 106 connected to ring 104 by a number of struts or rod stubs 108. Struts or stubs 108 extend parallel to a longitudinal axis 110 of the pusher device 100. Push rods 102 are angularly equispaced about a perimeter or edge 112 of ring 104 at locations that permit an insertion of the rods into respective deployment tubes 76 of delivery device 68.

Figure 19:
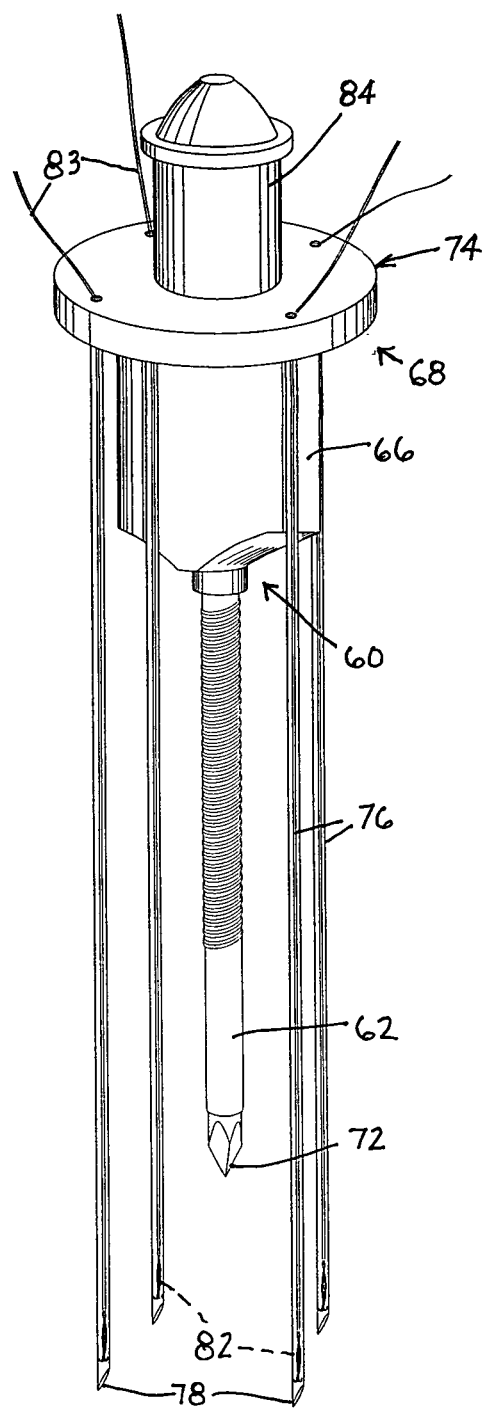
FIG. 19 is a perspective view of the fastener delivery assembly of FIG. 16 inserted into the cannula of FIG. 15.

FIG. 19 shows fastener or anchor delivery device 68 (FIG. 16) removably joined with cannula 60 (FIG. 15). Trocar 70 traverses cylinder 66 and tubular member 62 of cannula 60. To that end, a handle or gripper 114 at a proximal end of cannula 60 is provided with a bore 116 larger than an outer diameter of trocar 70. Cylinder 66 is likewise provided with a bore (not shown).

As shown in FIG. 19, disk or plate 74 of delivery device 68 rests on an upper shoulder or surface 117 (FIG. 15) of cylinder 66. Deployment tubes 76 extend parallel to trocar 70 and concomitantly parallel to tubular cannula member 62. Handle 84 of delivery device 68 is hollow and encloses gripper 114 of cannula 60.

Figure 20:
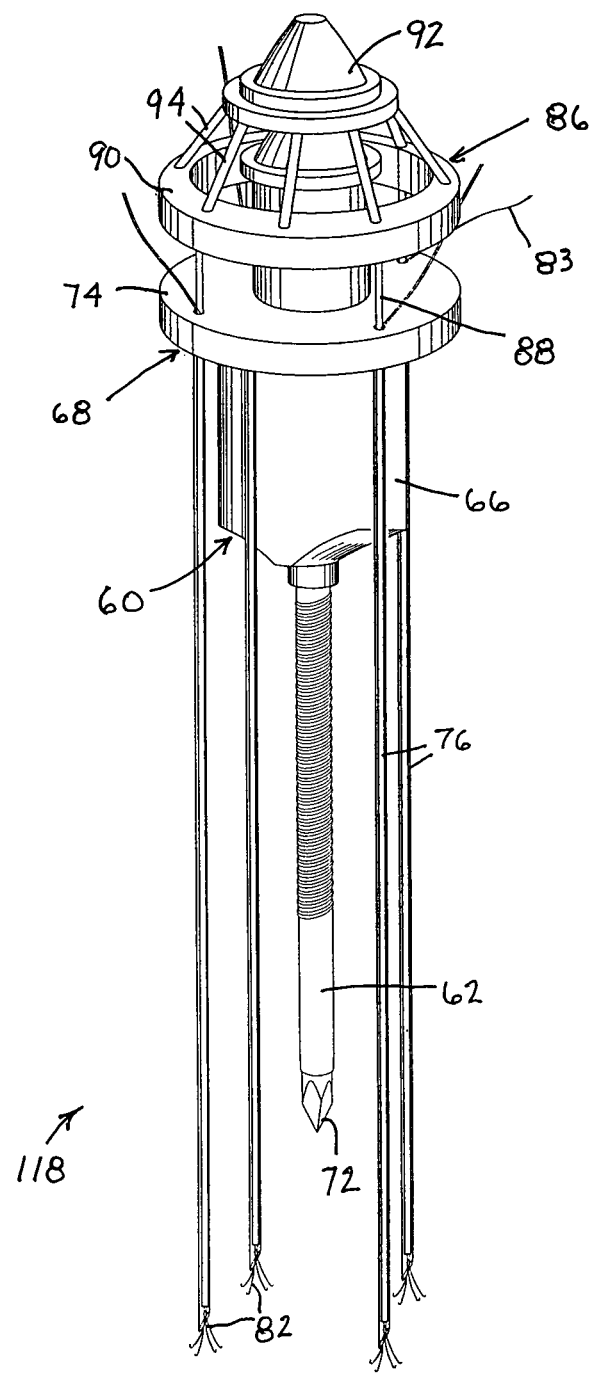
FIG. 20 is a perspective view similar to FIG. 19, showing also the pusher device of FIG. 17 in an operative configuration.

FIG. 20 illustrates a completed fastener delivery assembly 118 including delivery device 68 and pusher device 86 mounted to cannula 60. Push rods 88 of pusher device 86 are inserted through plate 74 of delivery device 68 into deployment tubes 76. FIG. 20 shows anchors 82 starting to emerge from the distal ends of deployment tubes 76 under a distally directed ejection stroke of pusher device 86. Anchors or fasteners 82 emerge simultaneously from the distal ends of deployment tubes 76, although optionally, push rods 88 and/or deployment tubes 76 may be designed to result in a temporally staggered ejection of the anchors or fasteners 82 from tubes 76.

Figure 21:
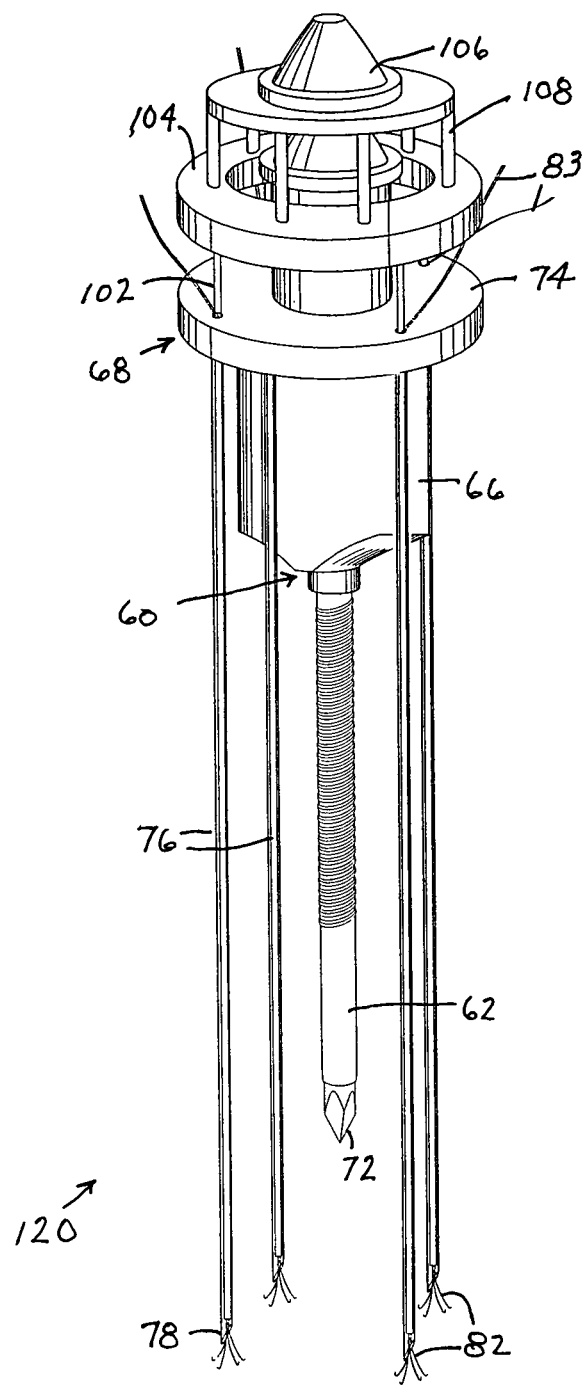
FIG. 21 is a perspective view similar to FIG. 19, showing also the pusher device of FIG. 18 in an operative configuration.

FIG. 21 similarly illustrates a completed fastener delivery assembly 120 including delivery device 68 and pusher device 100 mounted to cannula 60. Push rods 102 of pusher device 100 are inserted through plate 74 of delivery device 68 into deployment tubes 76. Anchors or fasteners 82 are shown as emerging from the distal ends of deployment tubes 76 under a distally directed ejection stroke of pusher device 100.

Figure 22:
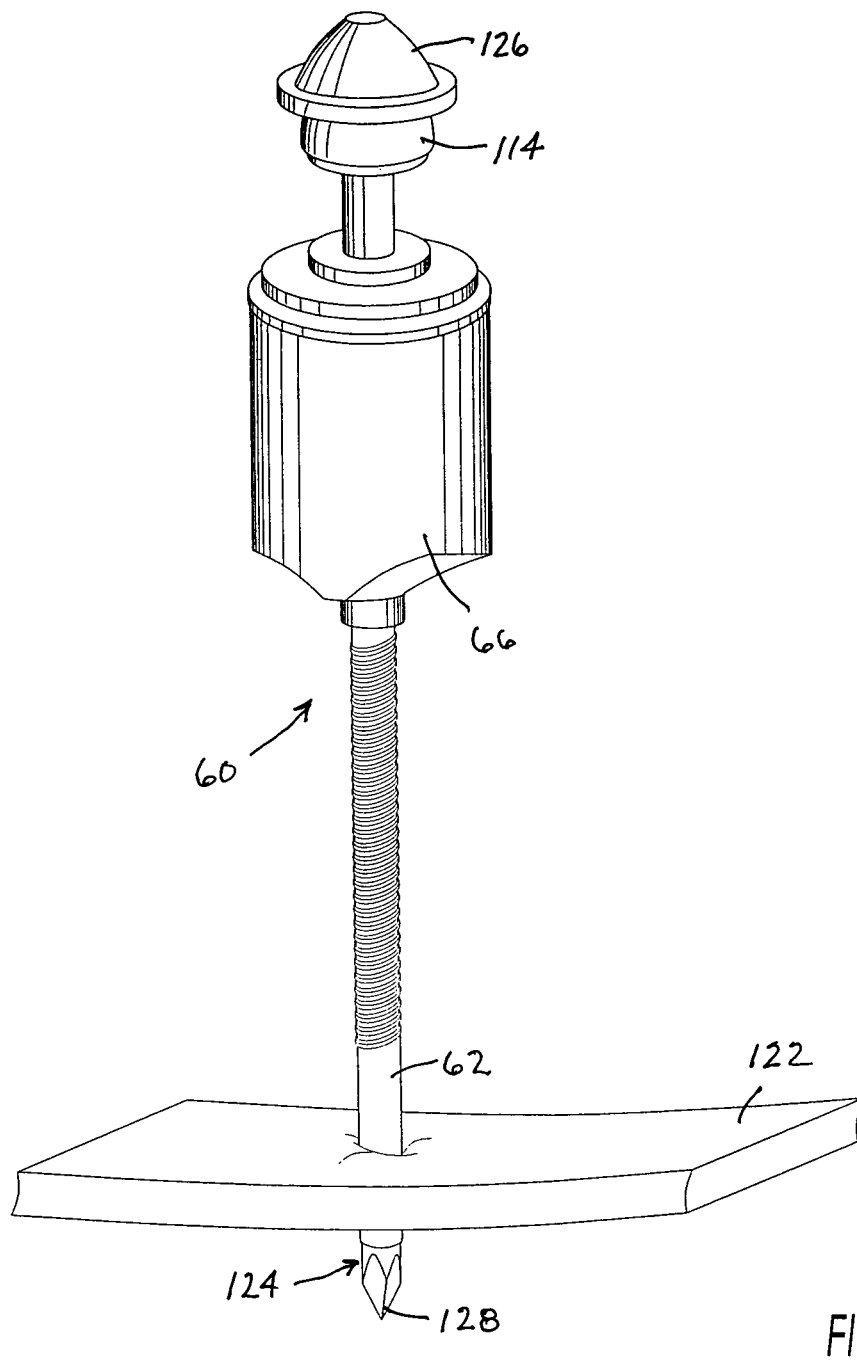
FIG. 22 is a perspective view of the cannula device of FIG. 15, with a trocar traversing same and piercing through tissue.
Figure 23:
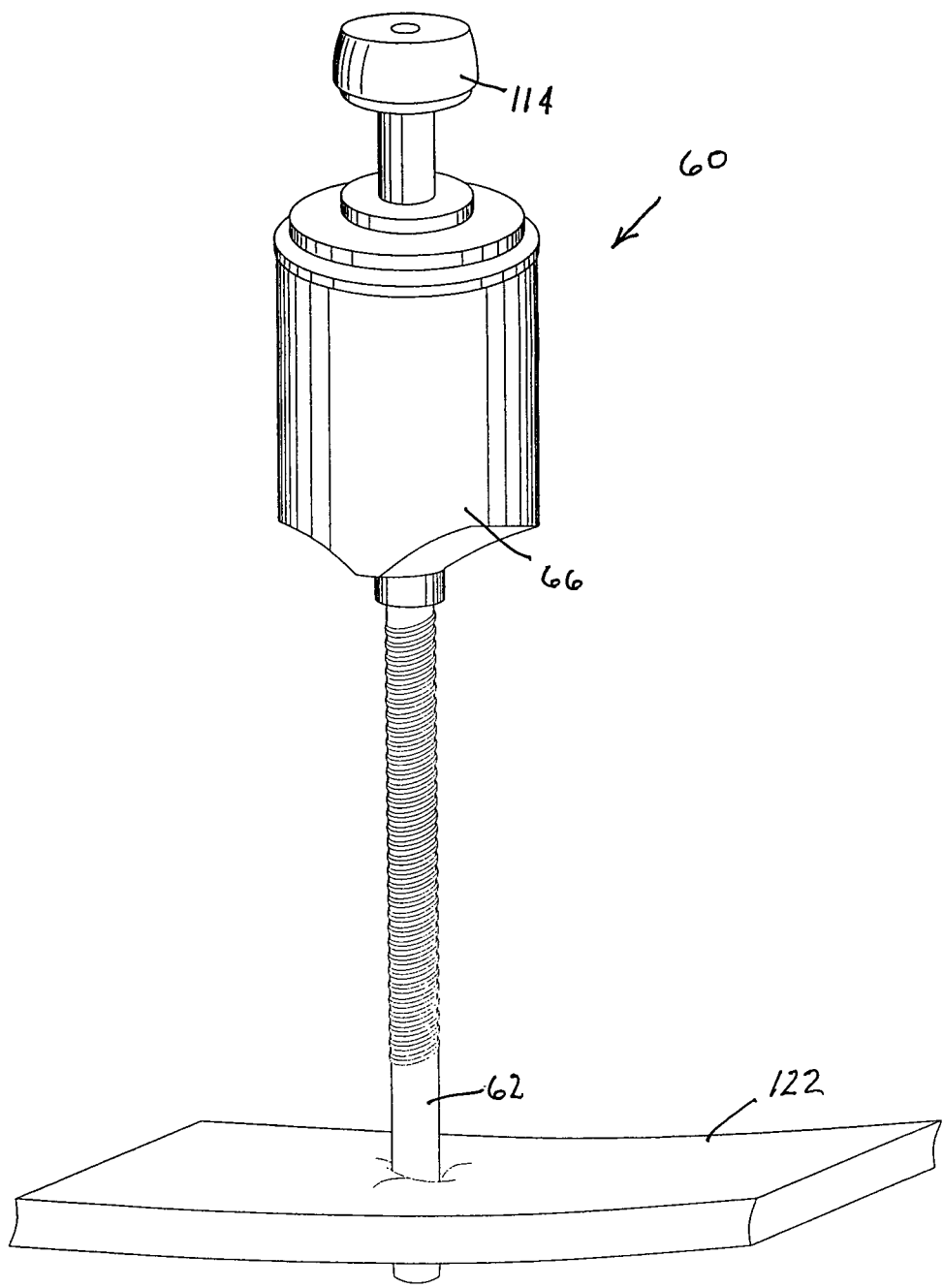
FIG. 23 is a perspective view similar to FIG. 22, showing the cannula placed through tissue, after the trocar has been removed.
Figure 24:
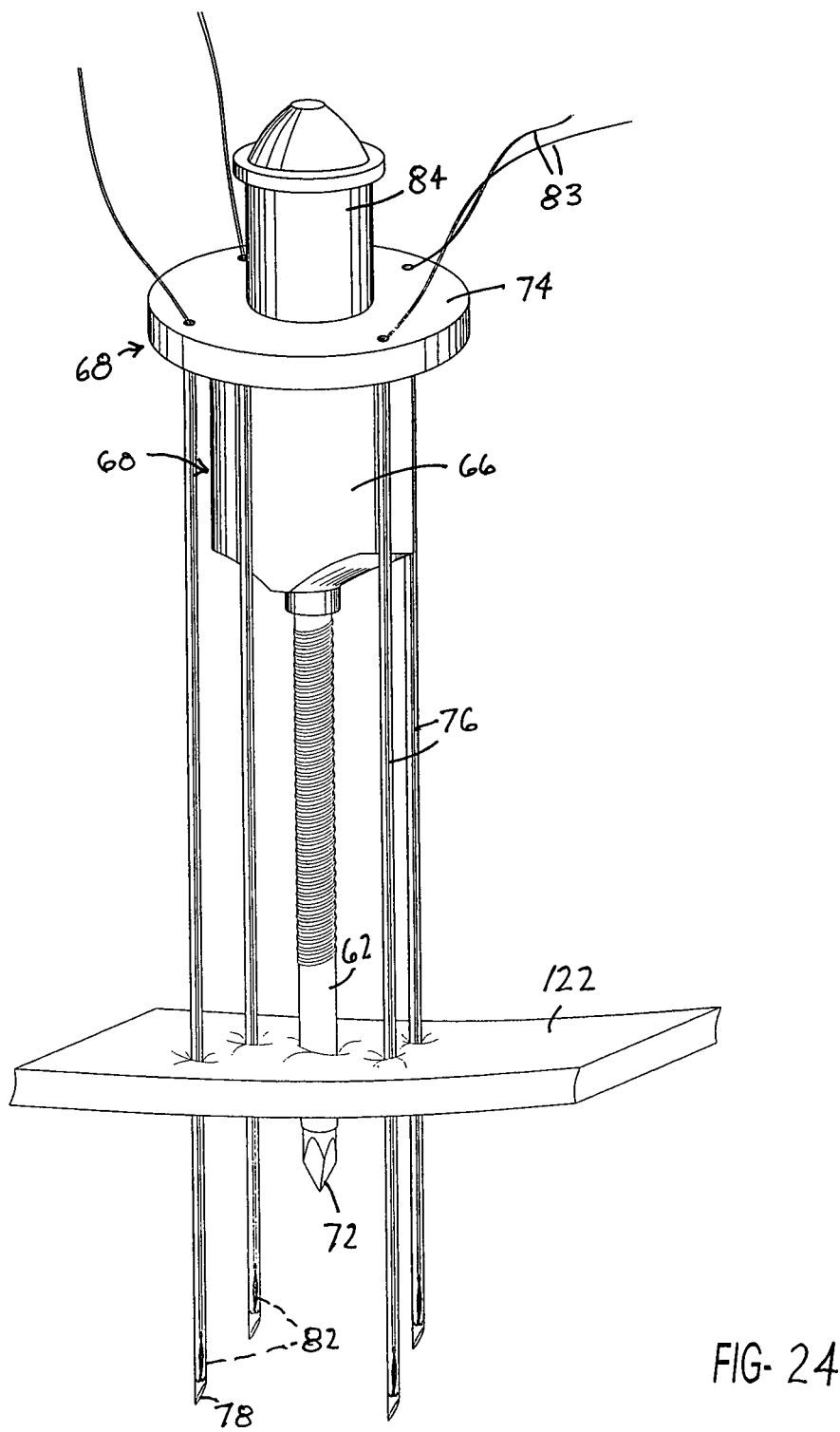
FIG. 24 is a perspective view of the multiple-fastener delivery assembly of FIG. 16 with the trocar thereof inserted through the cannula of FIG. 23.

During an interactive or other surgical procedure, cannula 60 is deployed in tissues 122 of a patient, as depicted in FIG. 22, by means of a trocar 124. Pushing on a handle end 126 of trocar 124, a surgeon pushes a sharp distal tip 128 of trocar 124, together with a distal end portion of cannula member 62, through tissues 122. Trocar 124 is then removed from cannula 60, as shown in FIG. 23. Subsequently, delivery device 68 is joined with the deployed cannula 60 (FIG. 24). More specifically, trocar 70 is centered with respect to cannula 60, so that trocar 709 is aligned with cannula member 62. Then delivery device 68 is moved towards the patient, with sharp tips 78 of needle-like deployment tubes 76 piercing the patient's tissues 122 on different sides of an incision or perforation 130 traversed by cannula member 62.

Figure 25:
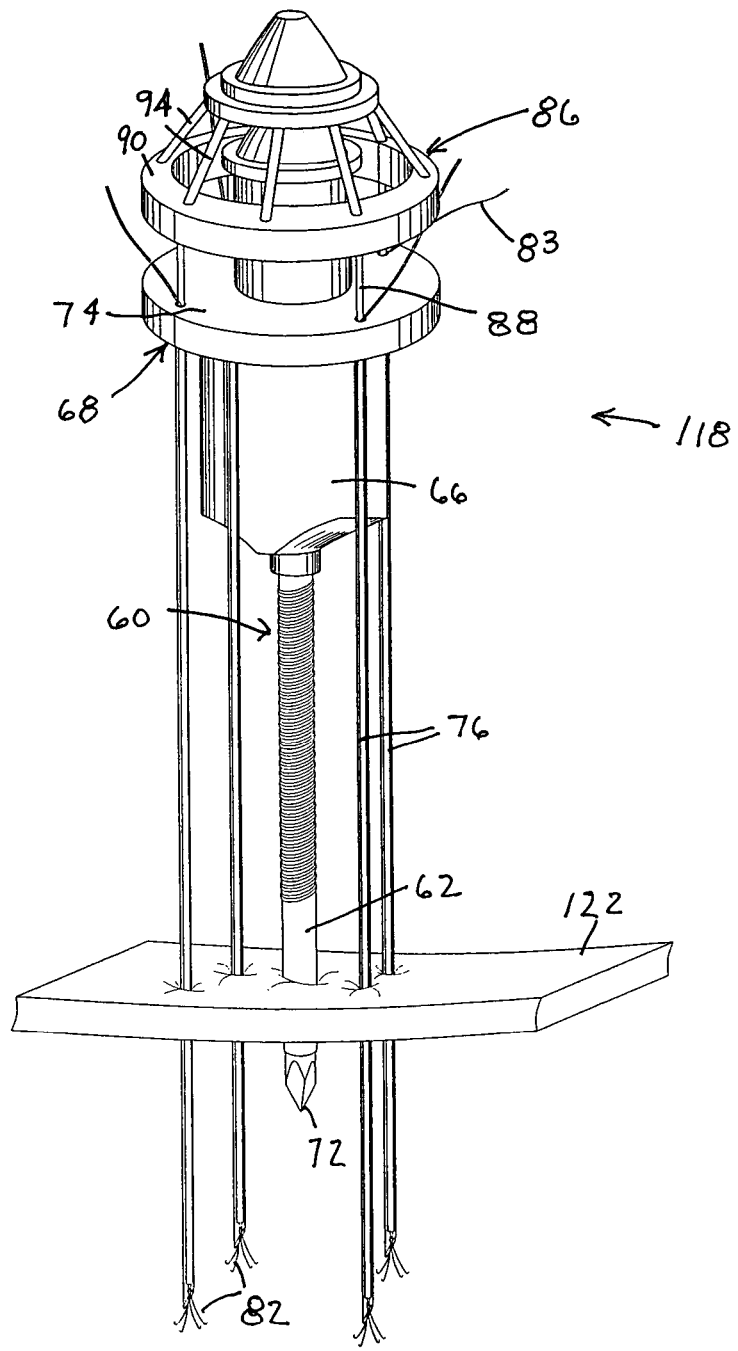
FIG. 25 is a perspective view similar to FIG. 24, showing the pusher embodiment of FIG. 17 positioned for pushing anchors or fasteners out of respective needle-like tubular bodies of the multiple-fastener delivery assembly.

FIG. 25 show a subsequent step in a surgical closure procedure wherein pusher device 86 is connected to fastener delivery device 68 such that push rods 88 are inserted into anchor deployment tubes 76 and such that the pusher device has been shifted far enough in the distal direction (towards the patient) that anchors or fasters 82 emerge from the distal end of deployment tubes 76 and expanded from the closed insertion configuration to an opened use configuration wherein wires or spines (not designated) of the anchors splay outwardly for facilitating the catching of the anchor in the target tissue at the surgical site.

Figure 26:
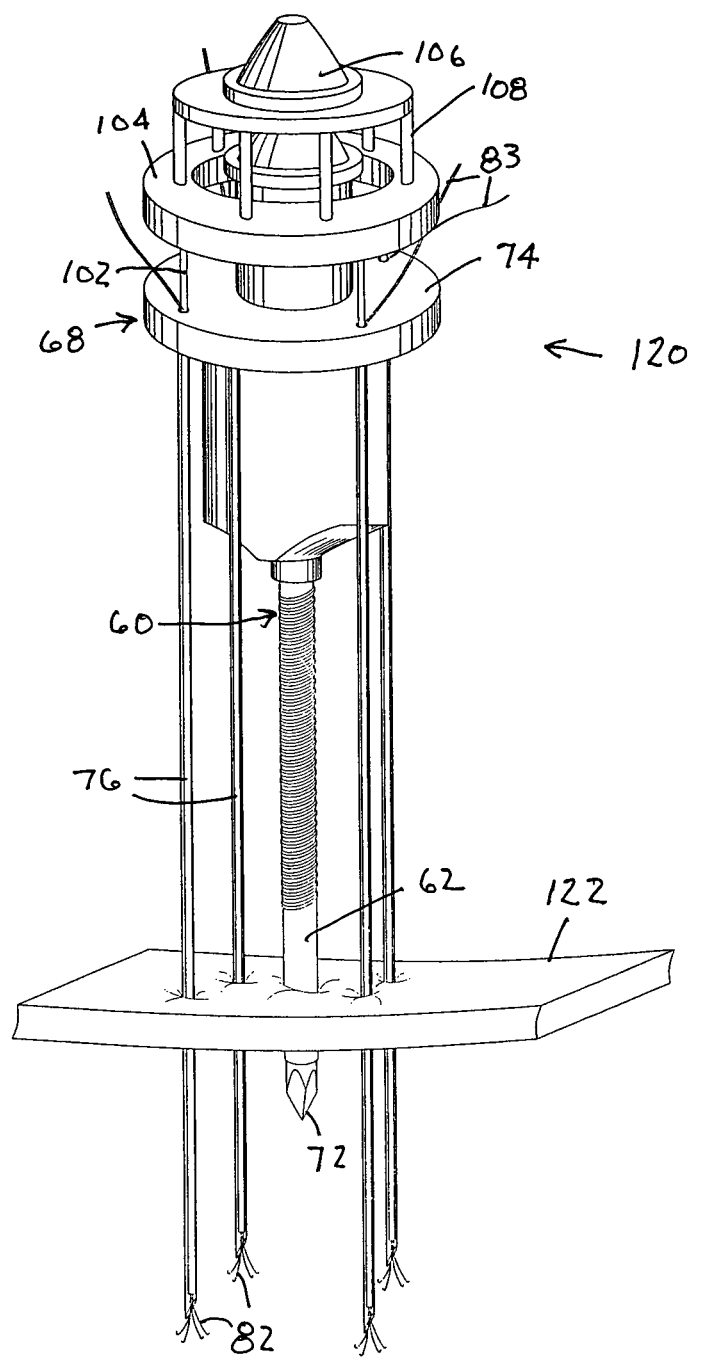
FIG. 26 is a perspective view similar to FIG. 25, showing the pusher embodiment of FIG. 18 in place of the pusher embodiment of FIG. 17.

FIG. 26 is similar to FIG. 25 except that pusher device 100 is used instead of pusher device 86.

Figure 27:
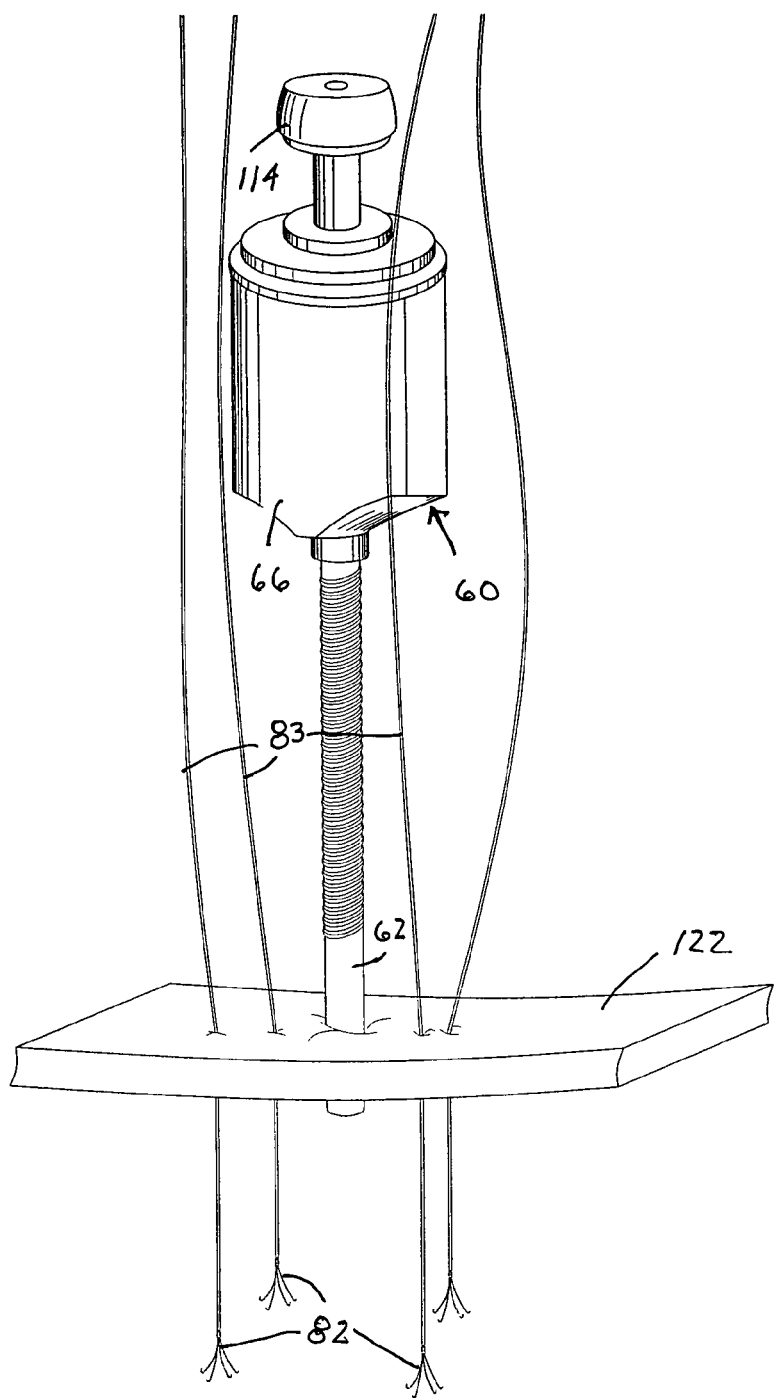
FIG. 27 is a perspective view of the cannula of FIG. 23 with four anchors and respective suture threads after ejection thereof from the respective needle-like tubular bodies of the multiple-fastener delivery assembly and after removal of the multiple-fastener delivery assembly.
Figure 28:
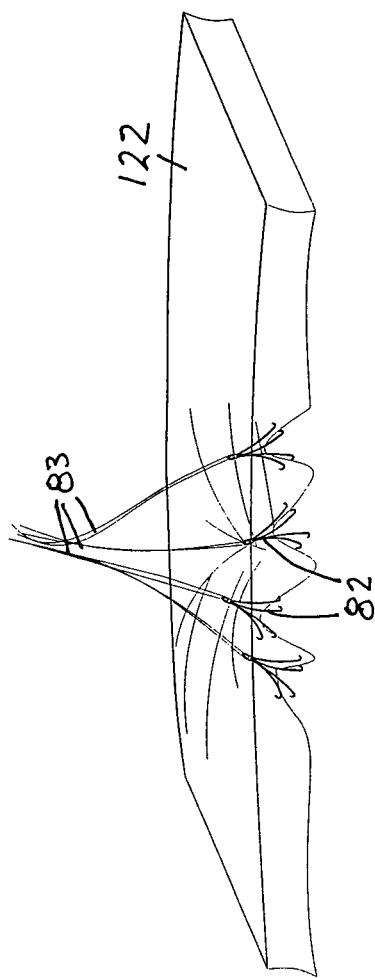
FIG. 28 is a perspective view of the suture threads of FIG. 27 after the threads have been pulled and fastened together in order to close a puncture hole formed by the trocar and cannula of FIG. 22.

In a subsequent step of the surgical closure procedure, delivery device 68 together with pusher device 86 or 100 is removed from the patient and from cannula 60. Suture threads 83 then extend from the patient (FIG. 27). As illustrated in FIG. 28, suture threads 83 are then cinched together, for instance, by tying or by the use of a locking device (not shown). The cinching of the suture threads 83 approximates the tissue about incision or perforation 130 and thereby closes the incision or perforation.

Figure 29:
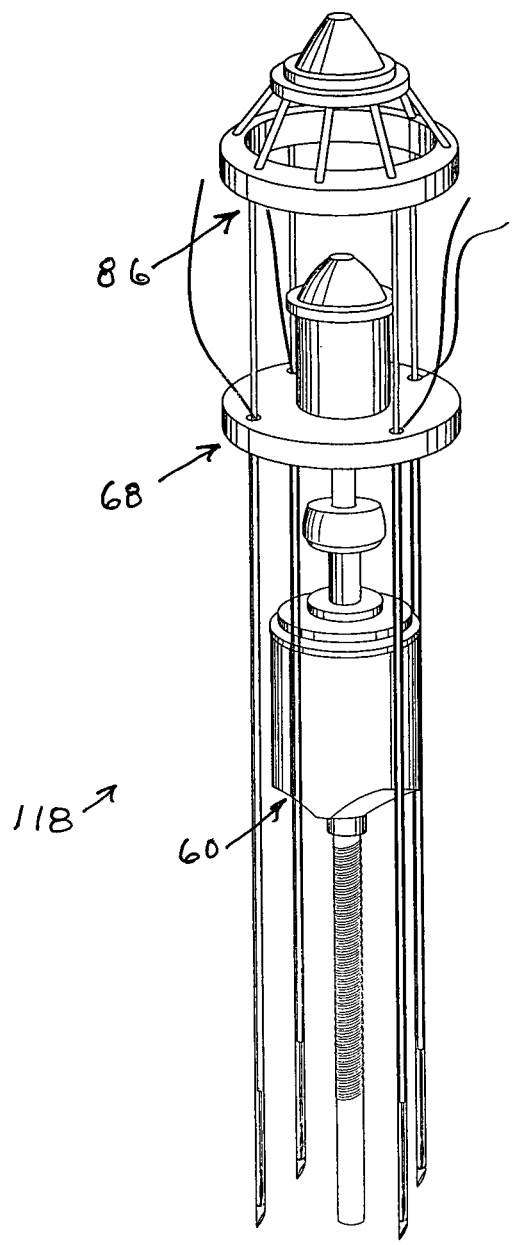
FIG. 29 is a perspective view of a surgical fastening assembly in accordance with the present invention, including a cannula, an anchor delivery assembly, and a pusher.
Figure 30:
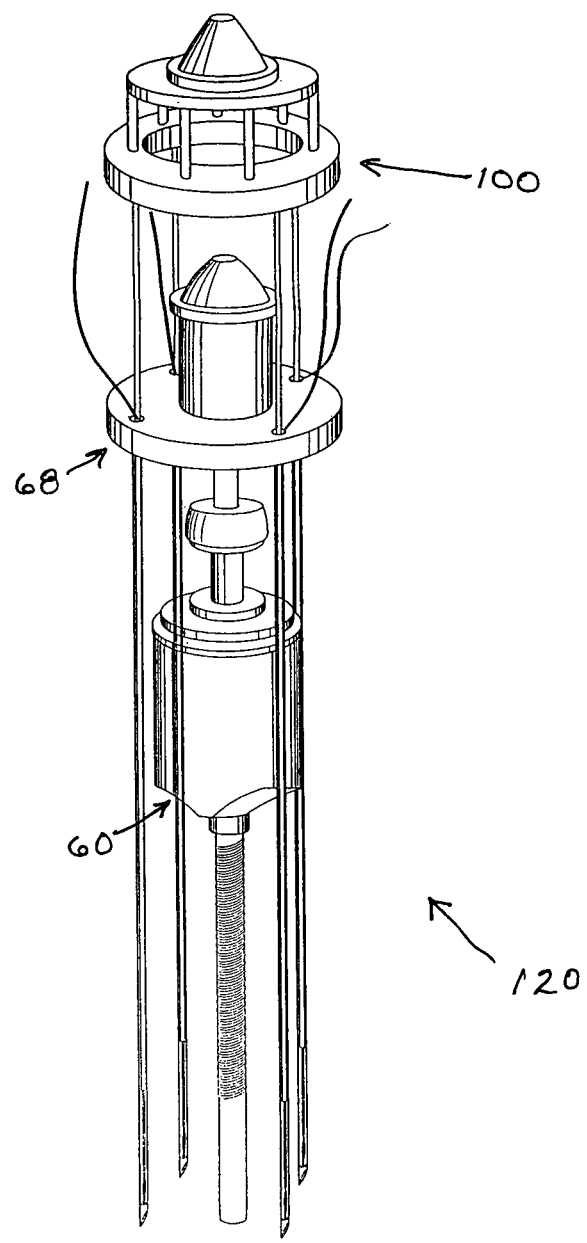
FIG. 30 is a perspective view of another surgical fastening assembly in accordance with the present invention, including a cannula, an anchor delivery assembly, and a pusher.

FIG. 29 shows surgical fastening assembly 118 with cannula 60, delivery device 68 and pusher device 86 slid apart from one another for clarity. FIG. 30 likewise shows surgical fastening assembly 120 with cannula 60, delivery device 68 and pusher device 100 slid apart from one another.

Figure 31:
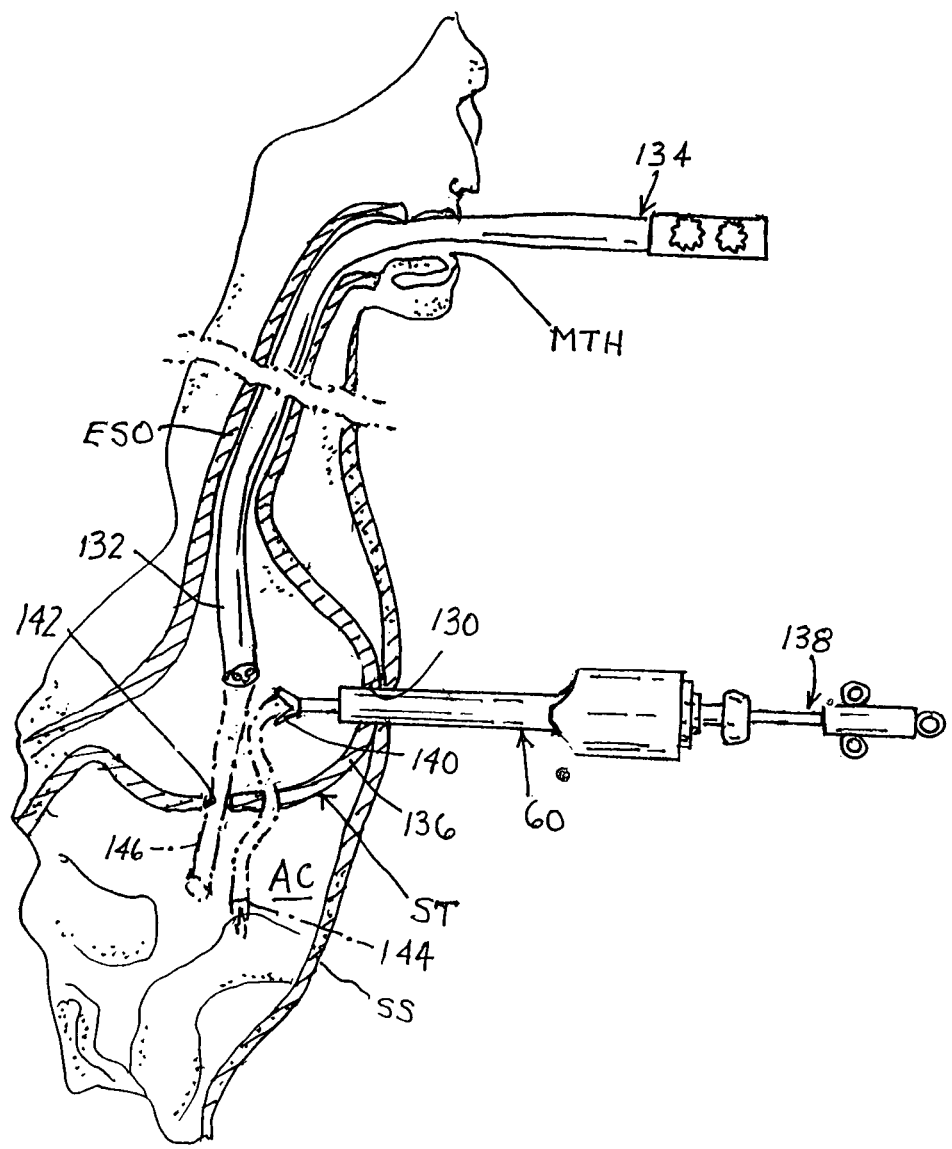
FIG. 31 is a schematic cross-sectional view of a human subject, showing a combined endoscopic and trans-abdominal surgical procedure.

Perforation or incision 130 may be located in a wall of a hollow internal organ of the patient, such as the stomach wall. In that case, the pushing of deployment tubes 76 may include inserting the distal end portions of tubes through the stomach wall, and anchor 82 engage the wall along one side thereof. The distal end portions of deployment tubes 76 are likewise inserted though an external skin surface prior to inserting it through the stomach wall. As illustrated in FIG. 31, such a procedure may be performed in interactive endoscopic surgery, comprising both endoscopic processes and procedures carried out through the abdominal wall.

As depicted in FIG. 31, a flexible distal end portion 132 of an endoscope 134 in inserted into stomach ST through the mouth MTH, a natural body opening, and the esophagus ESO. The forming of perforation or incision 130 in stomach wall 136 may then be performed under visual observation afforded by endoscope 134. After the formation of perforation or opening 130 in stomach wall 136, a distal end portion of a flexible or rigid laparoscopic instrument 138, with an operative tip 140 is passed into the stomach ST through perforation or incision 130 and cannula 60. Naturally, this procedure entails insertion of the distal end portion of instrument 138 through an external skin surface SS of the patient. Surgical instrument 138 is actuated from outside the patient, i.e., extracorporeally, to perform a surgical procedure at a selected surgical site inside the patient. That surgical site may be inside the stomach ST or, for example, inside the patient's abdominal cavity AC and outside of the stomach ST. In the latter case, at least one other perforation or incision 142 is formed in the stomach wall 136 to permit the passage of the distal end portions of surgical instrument 138 and endoscope 134 into the abdominal cavity AC, as indicated in phantom lines 144 and 146. Endoscope 134 is operated to view the surgical site during the actuating of surgical instrument 138.

Figure 32A:
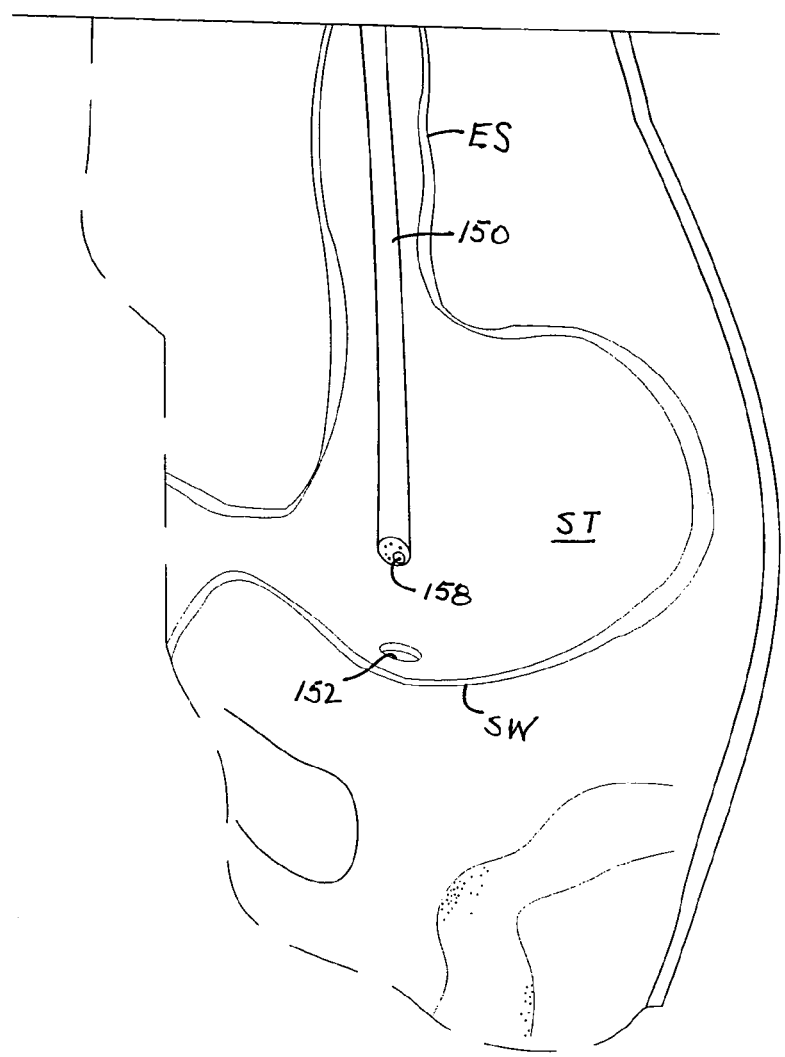
FIGS. 32A through 32G are schematic cross-sectional views of a person's stomach, showing successive steps in an endoscopically mediated surgical closure procedure in accordance with the present invention.
Figure 32B:
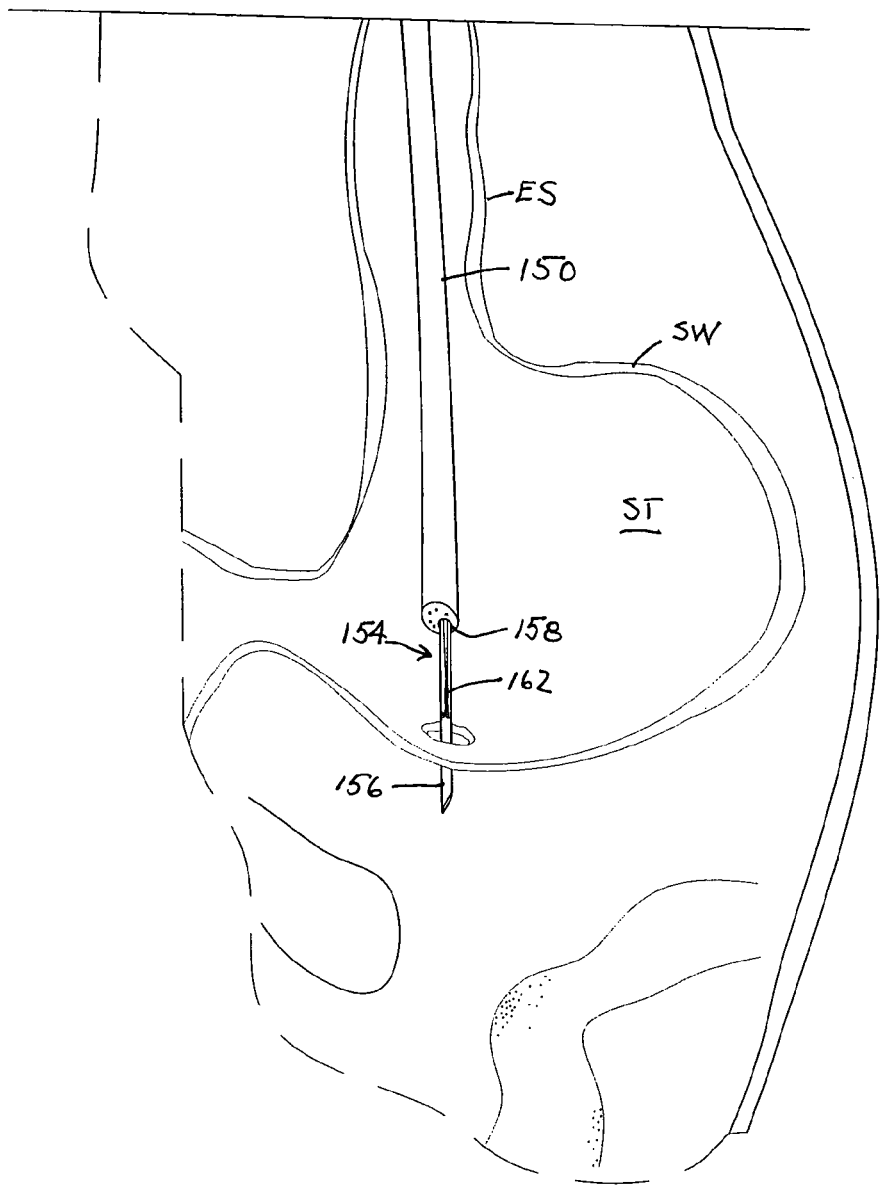
Figure 32C:
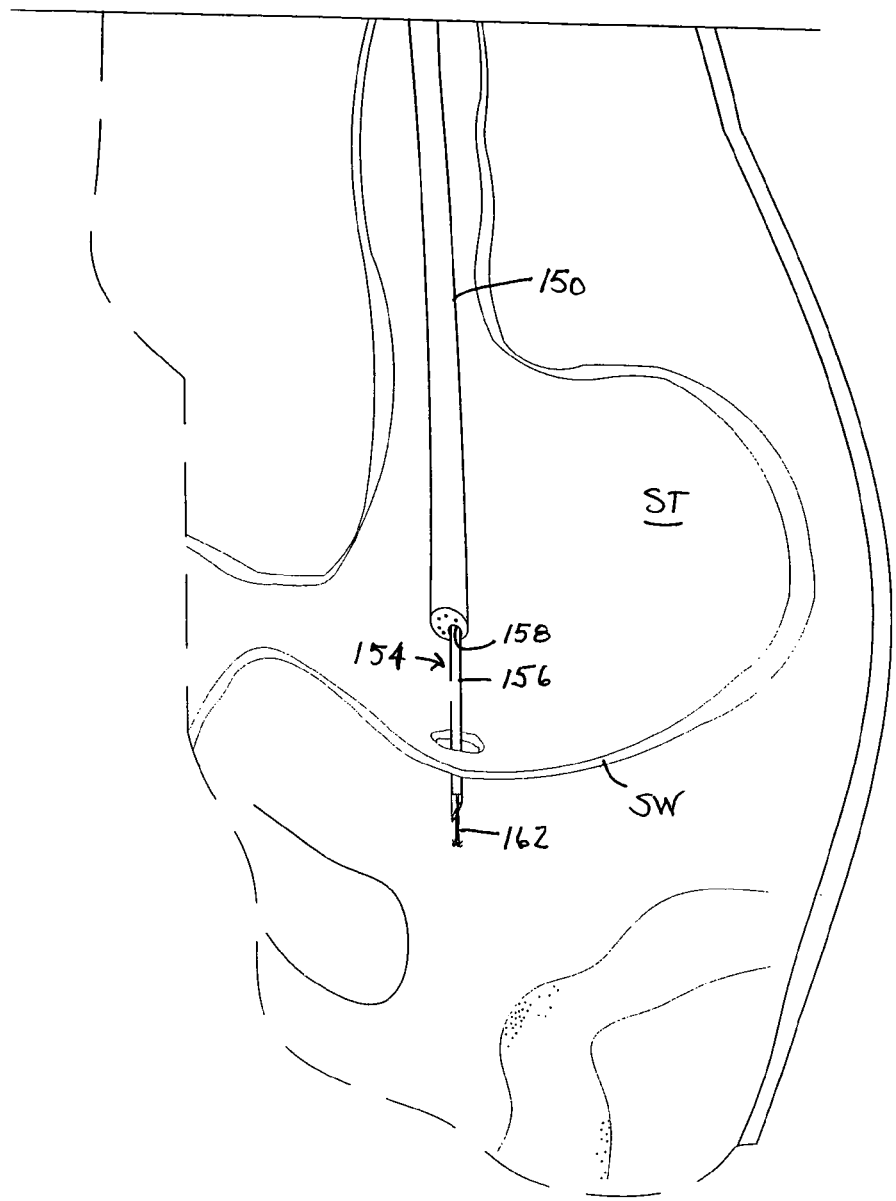
Figure 32D:
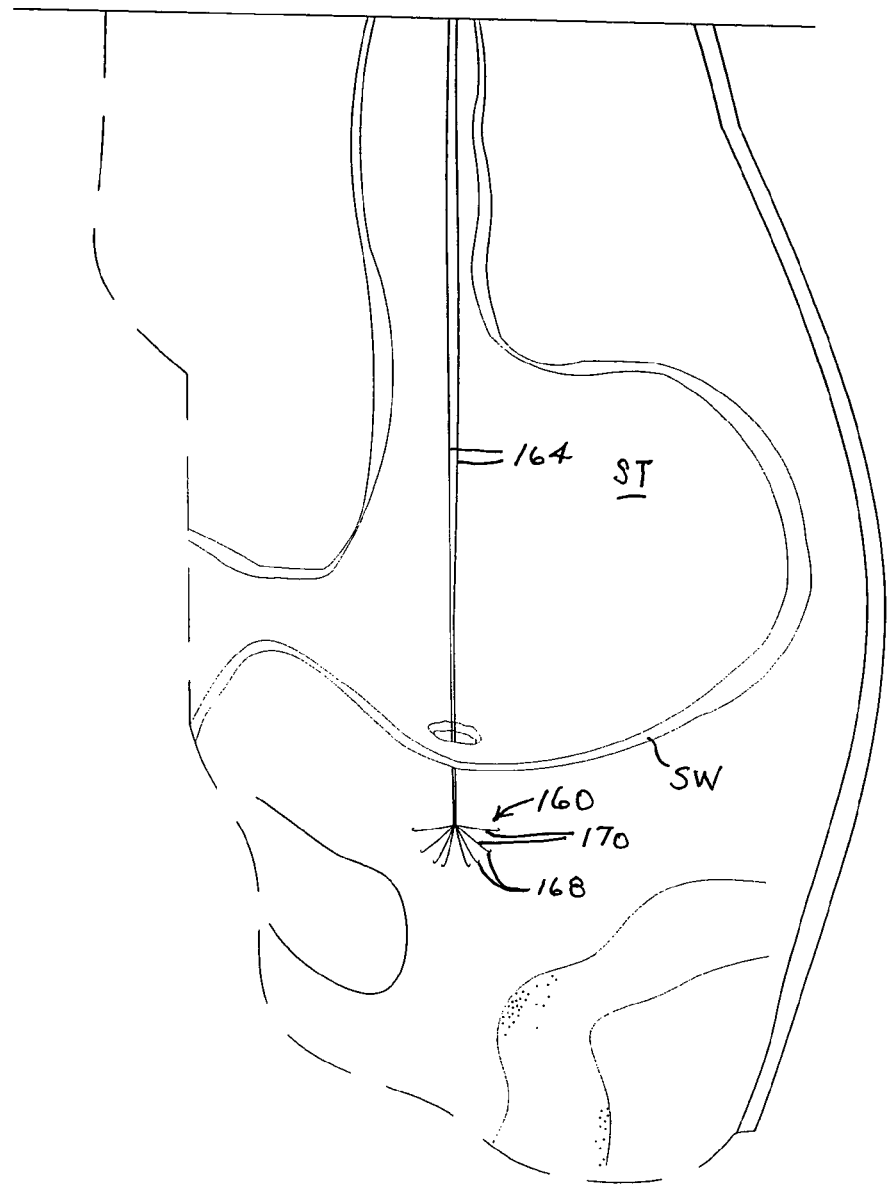
Figure 32E:
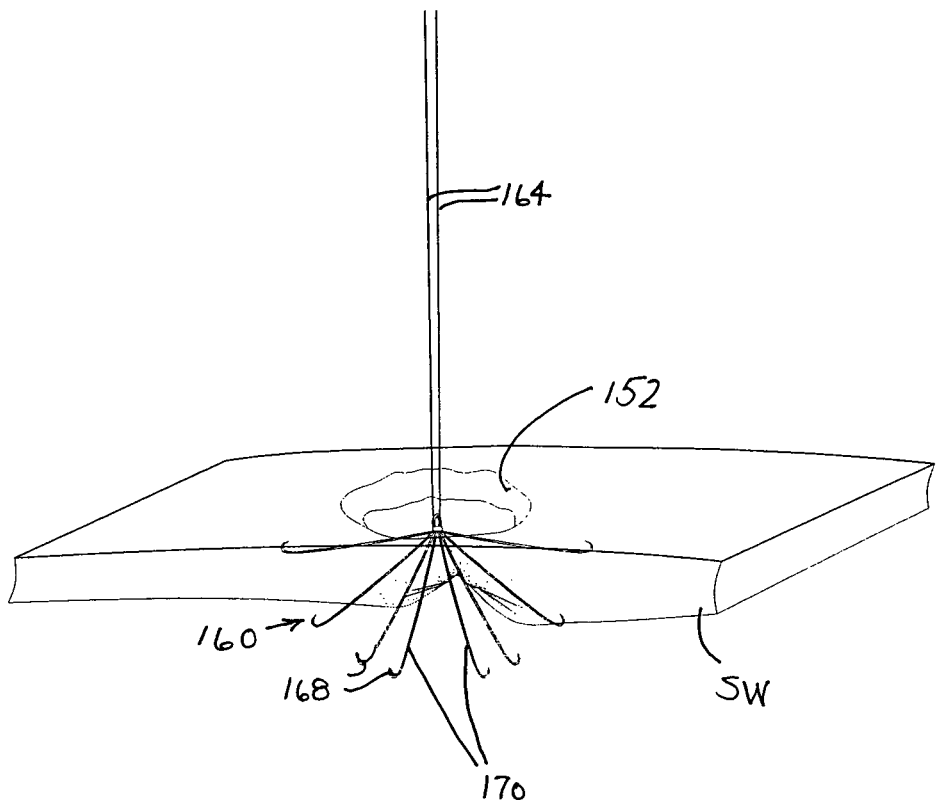
Figure 32F:
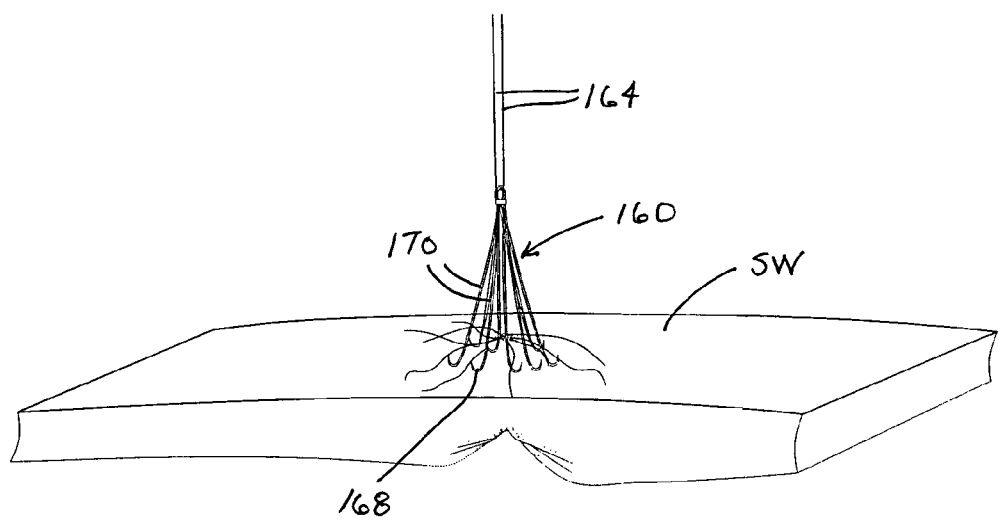
Figure 32G:
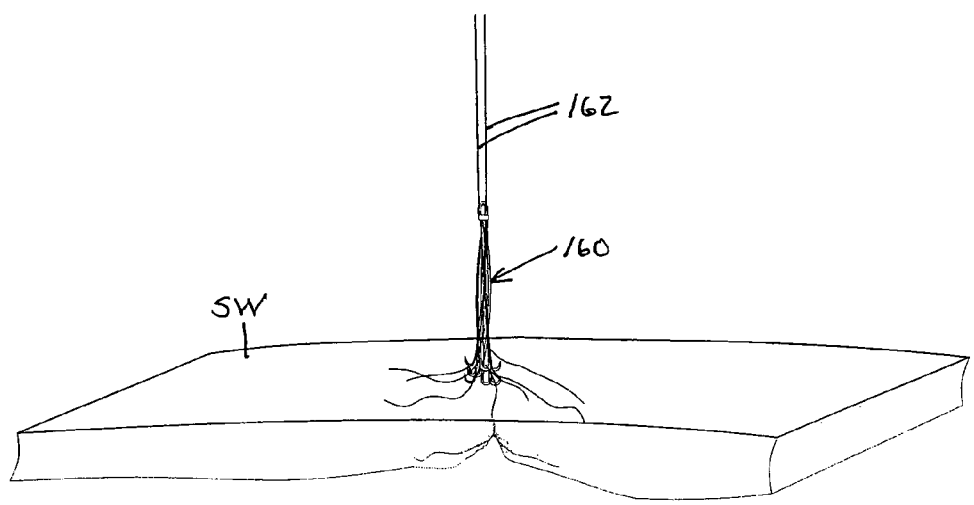

FIGS. 32A through 32G are schematic partial cross-sectional views of a person's abdomen, showing successive steps in a closure procedure in accordance with the present invention. FIG. 32A shows a flexible shaft 150 of an upper-GI endoscope inserted into a patient's stomach ST through the esophagus ES. An incision has been made in a lower portion of the stomach wall SW to form an aperture or opening 152 leading to the peritoneal or abdominal cavity PC. To close the aperture or opening, a closure device 154 is deployed via the endoscope. More particularly, a distal end portion of tubular sheath 156 is introduced into the stomach ST and through opening 152 via a working channel 158 of endoscope shaft 150, as shown in FIG. 32B. Subsequently, an anchor 160 disposed in a closed configuration 162 inside tubular sheath 156 (FIG. 32B) is ejected from a distal end of the sheath into peritoneal cavity PC (FIG. 32C). Owing to internal spring forces, possibly temperature dependent, anchor 160 opens from the closed configuration FIGS. 32B and 32C) into an expanded grappling hook configuration (FIG. 32D). Endoscope shaft 150 may be withdrawn from the stomach ST through esophagus ES at this juncture, as indicated in FIG. 32D et seq. Preferably, however, the distal end portion of the endoscope is maintained in the stomach to enable visual monitoring of subsequent steps in the closure procedure. As shown in FIG. 32E, a two-strand suture thread 164 attached to a proximal or apex end of anchor 160 is pulled in a proximal direction (through the patient's mouth, not shown), as indicated by an arrow 166, thereby bringing hooks 168 at the distal end of anchor legs 170 into engagement with stomach wall SW. Further pulling of suture strands 164, with stomach wall SW about opening 152 entrained by anchor 160, closes the opening. FIG. 32F shows the opening substantially closed, while FIG. 32G shows the opening tightly closed. During the closure operation, anchor legs 170 are collapsed towards one another so that the anchor assumes an at least partially closed deployed configuration holding the tissues of stomach wall SW about opening or perforation 152 in approximation to one another.

If necessary, another anchor (not shown) may be placed in stomach wall SW and coupled tightly to suture strands 164 to maintain tension on anchor 160. Such an anchor may be placed in a tented or folded portion of the inner stomach wall in a procedure conducted via endoscope shaft 150.

In a modified method of closing a gastric perforation, one or more anchors 160 are implanted prior to creating the gastric perforation. Endoscope 150 is inserted through the esophagus ES into the stomach ST and a full upper gastrointestinal endoscopic examination is performed. The endoscope is pulled back from the duodenum, and with the stomach ST fully insufflated, the endoscope is pointed in an anterior direction to identify a suitable entry site of a needle housing the anchors. With light from the endoscope transluminating the abdominal wall, a second operator (a medical specialist) indents the site of maximal light transillumination. The site is pierced under endoscopic visualization using an 18 gauge anchor-housing needle.

A flexible grasping device (prototype) is passed through a working channel of the endoscope, and a rugal fold, preferably located along the inferior aspect of the greater curvature is grasped, and tented. The needle operator aims the needle under endoscopic viewing towards the tented fold and pierces clear through it. The endoscope operator releases the grasper's hold and grasps a second rugal fold about 2 cm away from the exit point of the needle, upon which the needle operator pierces the second tented fold. The grasper is released, and withdrawn. Now the anchor-pusher is introduced into the needle, and advanced until the Nitinol (NiTi) anchor, attached to a 3-0 silk suture thread, exits the needle's distal end. Pusher and needle are withdrawn, and the anchor remains in the stomach, its suture thread exiting the abdominal wall.

A second needle is introduced in the same fashion as above, about 3 cm away from the suture thread's exit abdominal wall-exit point, and another anchor is deposited with two needle stitches. The second intragastric exit point of the second needle is about 1 cm away from the first anchor. When the second needle is pulled out, two anchors with their respective suture threads are deposited along the lower (dependant) aspect of the greater curvature. Now the gastric incision is performed as described above, and the endoscope is introduced through it into the peritoneal cavity, with the guidewire leading the way. Air is insufflated through the endoscope distending the peritoneal cavity, and peritoneoscopy is performed.

When the intraperitoneal procedure is complete, the endoscope is withdrawn back into the stomach. As the stomach is collapsed, it cannot be distended because any air will escape through the gastric incision. However, upon a pulling on the extra-abdominal suture threads each attached to its respective anchor, the anchors hook into the gastric wall, and the gastric incision is closed, as evidenced by stomach distention with endoscopic air insufflation. The suture threads are then tied together, producing tight closure of the gastric incision.

Figure 33A:
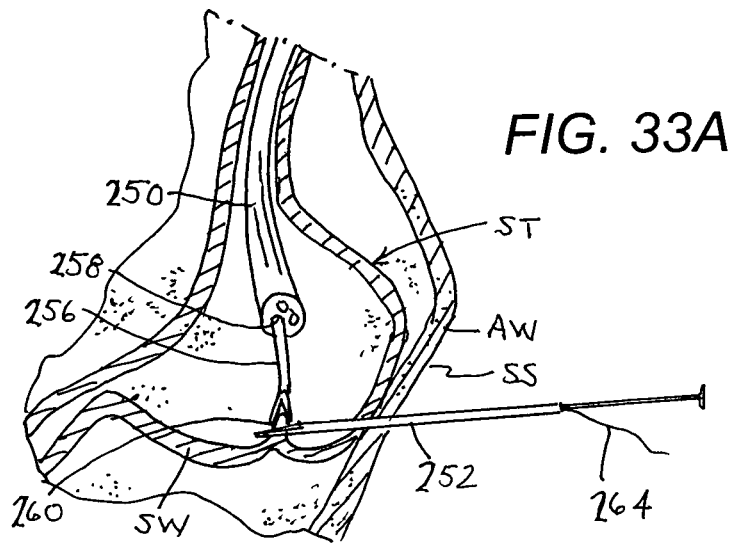
FIGS. 33A through 33F are schematic cross-sectional views of a person's stomach, showing successive steps in an endoscopically mediated surgical closure procedure in accordance with the present invention.

In a normal-orifice translumenal endoscopic surgical (NOTES) procedure, illustrated in FIG. 33A et seq., a distal end portion 250 of an endoscope is introduced into a hollow organ such as the stomach ST. The stomach is insufflated, whereupon one indents the stomach ST by pressing on the abdominal wall AW, locating a point along the inferior aspect of the greater curvature. Endoscope 250 is operated from outside the patient to visualize this finger indentation from inside the stomach. Subsequently, a distal end portion (not separately labeled) of a hollow needle 252 containing a splayable anchor 254 in a collapsed configuration is inserted through an external skin surface SS of the abdominal wall AW and into the stomach ST (FIG. 33A). This needle 252 is much thinner than trocars and cannulas that are currently being used in laparoscopy. The operating surgeon or endoscopist then introduces a flexible grasper 256 through a working channel 258 of the endoscope 250 and manipulates the grasper to grasp some tissue portion 260 of the stomach wall SW to heap it up, to enable a passage of the distal end portion of the needle 252 through the stomach wall. (The grasper 256 and the needle 252 may be oriented at about 90 degrees with respect to each other, because the needle 252 is approaching the surgical site along the stomach wall SW from the abdominal wall AW, while the grasper 256 approaches through the scope 250.)

Figure 33B:
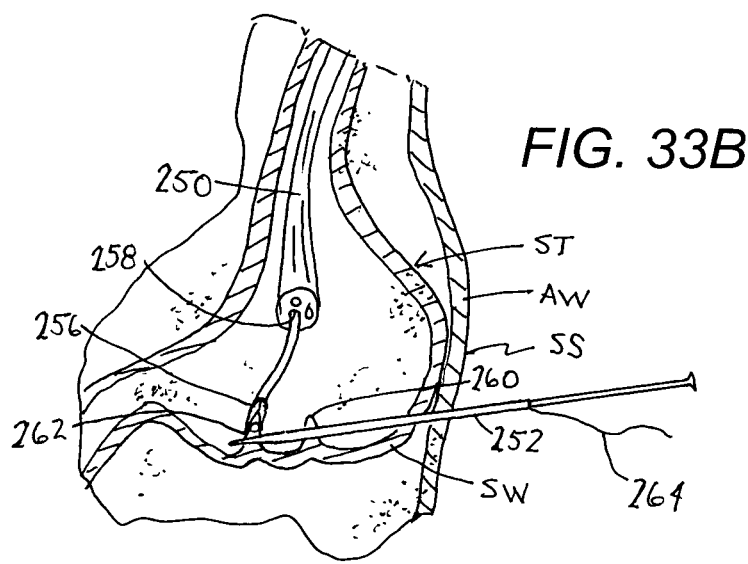
Figure 33C:
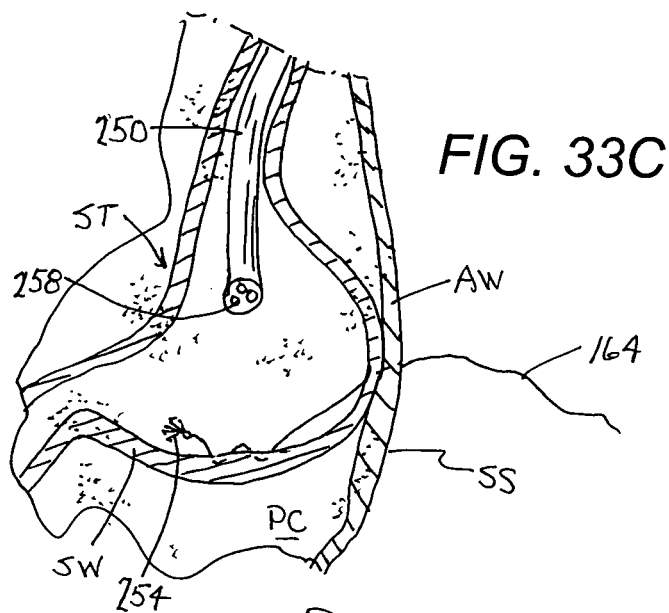

Grasper 256 is then operated from outside the patient, under visual guidance afforded by endoscope 250, to release tissue portion 260 and to grasp another bit of tissue 262 (FIG. 33B) a short distance away and to pull on that bit of tissue 262 to tent the stomach wall SW to facilitate a reintroduction of the needle 252 through this bit of tissue along the stomach wall. There are now two stitches in the wall of stomach ST, a short distance apart. At that juncture, anchor 254 is ejected from the distal tip of needle 252 (FIG. 33C). Needle 252 is then withdrawn from the patient, leaving a flexible line element 264 such as a suture thread extending through tissue portions 260 and 262 and loosely out through the stomach wall SW and the abdominal wall AW to an extracorporeal location (not designated). The surgeon or endoscopist then introduces another needle (not shown) carrying a second anchor 266, and repeats this stitching maneuver a few centimeters away from the first, on an opposite side of an intended surgical site along stomach wall SW. At the end of this procedure, there are two rows of stitches, one row in tissue portions 260 and 262 and another row in tissue portions 270 and 272, and two anchors 254 and 266 each with a respective entrained suture thread 264 and 274 extending out through abdominal wall AW to the extracorporeal location.

Figure 33D:
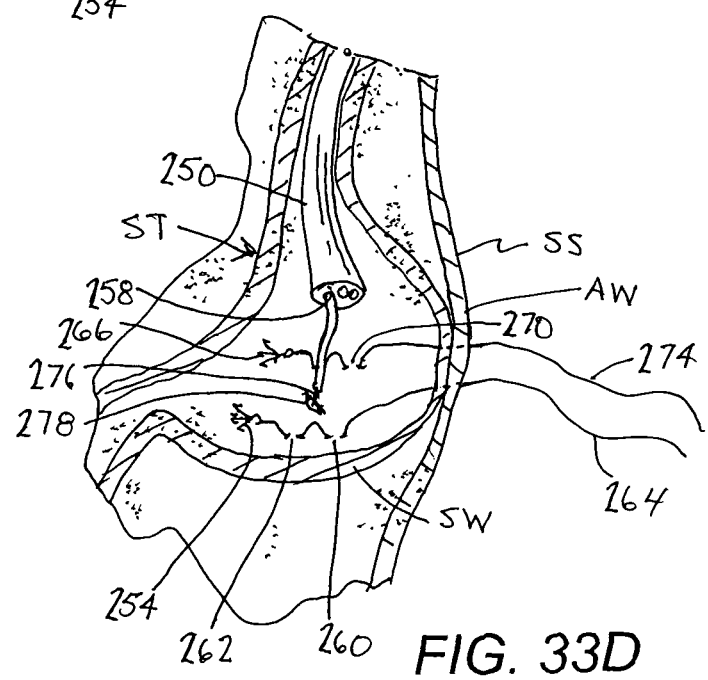
Figure 33E:
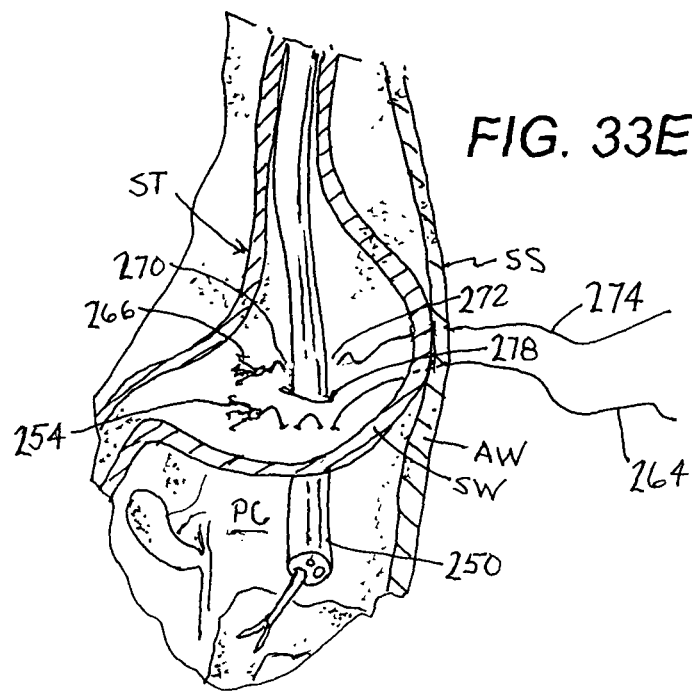

Subsequently, the surgeon or endoscopist inserts a cautery snare or a needle knife 276 through the working channel 258 of the endoscope 250 and makes an incision or perforation 278 at surgical site 268 for normal orifice translumenal surgery (NOTES) in between the two rows 260, 262 and 270, 272 of suture thread 264, 274 anchored in the stomach wall SW (FIG. 33D). (Anchors 254 and 266 and suture threads 264 and 274 are still laying loosely inside the stomach.) The distal end portion of scope 250 is inserted through incision or perforation 278 and thereupon a NOTES procedure is performed inside the peritoneal cavity PC (FIG. 33E). At the end of the procedure inside the peritoneal cavity PC, endoscope 250 is pulled back into the stomach ST. At that juncture the stomach ST is deflated and cannot be expanded by gas insufflation because all the gas escapes through the incision or perforation 278 in the stomach wall SW into the peritoneal cavity PC. With the stomach ST collapsed, there is no way to see how to implant the anchors to close the incision or perforation 278.

Figure 33F:
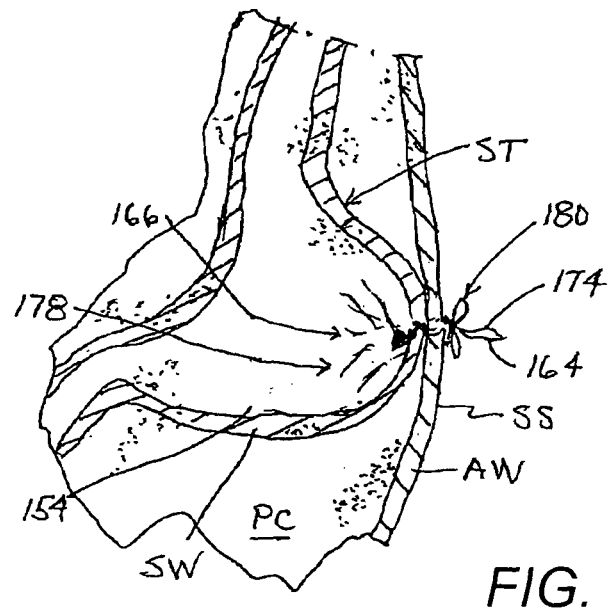

At this point, one pulls on flexible line elements or sutures 264, 274 from the extracorporeal location, to cinch the stomach wall SW in a region about incision 278 (FIG. 33F), thereby closing the incision and permitting the retention of an insufflation gas, to facilitate visual inspection via endoscope 250. The flexible line elements or sutures 264, 274 may be tied (for example, to one another in a knot 280) outside the patient, along skin surface SS.

Now, the above described method of hybrid suturing (meaning coming in with a straight needle through the abdominal wall AW, with grasper 256 and other flexible tools by the endoscopist and working at 90 degrees or so with one another) is easy to perform and may additionally facilitate the execution of other operations inside the stomach ST such as gastric restrictive surgery, bleeding or perforated ulcer repair, repair of leaks after bariatric surgery, fistulae repair etc.

The hollow tube that houses the anchors can also be a flexible tube that comes through the endoscope, and sewing can be carried out that way. If a grasper is required to first grasp the tissue, the procedure may be implemented through a split scope, or through a double channel scope.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A surgical fastening assembly to be used during rigid laparoscopic surgery only, comprising:
   a rigid cannula;
   a fastener delivery sub-assembly coupled to said cannula for use during laparoscopic surgery, said sub-assembly comprising a plurality of tubular needle members rigidly fixed to one another, said needle members being disposed parallel to one another in a first fixed predetermined array about a first central point or axis and at first predetermined distances with respect to one another about a longitudinal axis of the assembly;
   a plurality of fasteners disposable within said tubular needle members;
   a fastener-ejecting sub-assembly comprised of a plurality of rigid push members equal in number to said needle members, said push members being rigidly fixed to one another and disposed parallel to one another in a second fixed predetermined array about a second central point or axis and at second predetermined distances with respect to one another, said second fixed predetermined array corresponding to said first fixed predetermined array so that second central point is identical to the first central point and said second predetermined distances corresponding to respective ones of said first predetermined distances so that said push members are slidably disposable inside respective ones of said tubular needle members, thereby effecting ejection of said fasteners from said tubular needle members when said push members are shifted in a distal direction relative to said tubular needle members.

* * * * *